(12) United States Patent
Ushio et al.

(10) Patent No.: US 7,355,014 B2
(45) Date of Patent: *Apr. 8, 2008

(54) INTERFERON-γ INDUCING POLYPEPTIDE, PHARMACEUTICAL COMPOSITION THEREOF, MONOCLONAL ANTIBODY THERETO, AND METHODS OF USE

(75) Inventors: Shimpei Ushio, Okayama (JP); Kakuji Torigoe, Okayama (JP); Todao Tanimoto, Okayama (JP); Haruki Okamura, Osaka (JP); Masashi Kurimoto, Okayama (JP); Shigeharu Fukuda, Okayama (JP); Toshio Kunikata, Okayama (JP); Mutsuko Taniguchi, Okayama (JP); Keizo Kohno, Okayama (JP)

(73) Assignee: Kabushiki Kaisha Hay Ashibara Seibutsu Kagaku Kenkyujo, Okayama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/580,922

(22) Filed: Oct. 16, 2006

(65) Prior Publication Data

US 2007/0031403 A1 Feb. 8, 2007

Related U.S. Application Data

(60) Division of application No. 09/716,356, filed on Nov. 21, 2000, now Pat. No. 7,135,458, which is a continuation-in-part of application No. 08/832,180, filed on Apr. 8, 1997, now Pat. No. 6,214,584, which is a division of application No. 08/558,191, filed on Nov. 15, 1995, now abandoned, said application No. 09/716,356 is a continuation-in-part of application No. 08/974,469, filed on Nov. 20, 1997, now Pat. No. 6,207,641, which is a continuation of application No. 08/599,879, filed on Feb. 14, 1996, now abandoned, which is a continuation-in-part of application No. 08/558,190, filed on Nov. 15, 1995, now abandoned, said application No. 09/716,356 is a continuation-in-part of application No. 08/558,818, filed on Nov. 15, 1995, now Pat. No. 6,197,297, and a continuation-in-part of application No. 08/832,177, filed on Apr. 8, 1997, now Pat. No. 6,268,486, which is a division of application No. 08/558,818, filed on Nov. 15, 1995, now Pat. No. 6,197,297, said application No. 09/716, 356 is a continuation-in-part of application No. 08/832,198, filed on Apr. 8, 1997, now Pat. No. 6,242,255, which is a division of application No. 08/721,018, filed on Sep. 26, 1996, now abandoned.

(30) Foreign Application Priority Data

| Nov. 15, 1994 | (JP) | 1994/304203 |
| Feb. 23, 1995 | (JP) | 1995/58240 |
| Mar. 10, 1995 | (JP) | 1995/78357 |
| Sep. 18, 1995 | (JP) | 1995/262062 |
| Sep. 26, 1995 | (JP) | 1995/270725 |
| Sep. 29, 1995 | (JP) | 1995/274988 |
| Feb. 29, 1996 | (JP) | 1996/67434 |
| Sep. 20, 1996 | (JP) | 1996/269105 |

(51) Int. Cl.
- C07K 16/00 (2006.01)
- C07K 16/18 (2006.01)
- C07K 16/24 (2006.01)
- C12P 21/08 (2006.01)
- A61K 38/00 (2006.01)
- A61K 38/19 (2006.01)
- C07K 14/00 (2006.01)
- C07K 14/54 (2006.01)

(52) U.S. Cl. .......... 530/388.23; 530/350; 530/351; 530/388.1

(58) Field of Classification Search .......... None
See application file for complete search history.

(56) References Cited

U.S. PATENT DOCUMENTS

| 5,302,384 A * | 4/1994 | Gimbrone et al. ......... 424/85.2 |
| 6,197,297 B1 * | 3/2001 | Kunikata et al. ......... 424/156.1 |
| 6,509,449 B1 * | 1/2003 | Kunikata et al. ....... 530/388.23 |

OTHER PUBLICATIONS

Okamura et al., "Cloning of a new cytokine that induces IFN-gamma production by T cells," Nature, vol. 378 No. 6552, pp. 88-91 (Nov. 1995).*
Pati, "Novel vectors for expression of cDNA encoding epitope-tagged proteins in mammalian cells," Gene, vol. 114 No. 2, pp. 285-288 (May 1992).*

* cited by examiner

Primary Examiner—Zachariah Lucas
(74) Attorney, Agent, or Firm—Browdy and Neimark, PLLC

(57) ABSTRACT

A human IFN-γ inducing polypeptide and its nucleotide sequence was isolated, purified and characterized. Pharmaceutical compositions containing this novel INF-γ inducing polypeptide or active fragments thereof are formulated and monoclonal antibodies are raised against this polypeptide or antigenic fragments thereof. The polypeptide can be used in a method for treating diseases susceptive to treatment with INF-γ, and methods for enhancing the cytotoxicity of NK cells or for inducing the formation of LAK cells, such as to treat tumors and malignant pathologies.

1 Claim, 5 Drawing Sheets

MOLECULAR WEIGHT (DALTONS)　　MARKER　　LANE 1　　LANE 2

67k

45k

30k 20.1k 14.4k

INTERFERON-γ INDUCING POLYPEPTIDE, PHARMACEUTICAL COMPOSITION THEREOF, MONOCLONAL ANTIBODY THERETO, AND METHODS OF USE

CROSS-REFERENCE TO RELATED APPLICATIONS

This application is a divisional of application Ser. No. 09/716,356, filed Nov. 21, 2000, which is a continuation-in-part of: application Ser. No. 08/832,180, filed Apr. 8, 1997, which is a divisional of Ser. No. 08/558,191, filed Nov. 15, 1995, now abandoned; application Ser. No. 08/974,469, filed Nov. 20, 1997, which is a continuation of Ser. No. 08/599,879, filed Feb. 14, 1996, now abandoned, which application Ser. No. 08/599,879 is a continuation-in-part of Ser. No. 08/558,190, filed Nov. 15, 1995, now abandoned; application Ser. No. 08/558,818, filed Nov. 15, 1995; application Ser. No. 08/832,177, filed Apr. 8, 1997, which is a divisional of Ser. No. 08/558,818; and application Ser. No. 08/832,198, filed Apr. 8, 1997, which is a divisional of Ser. No. 08/721,018, filed Sep. 26, 1996, now abandoned. Each of the above-identified applications for which the present application is a continuation-in-part is incorporated entirely herein by reference.

BACKGROUND OF THE INVENTION

1. Field of the Invention

The present invention relates to a polypeptide and fragments thereof which induce interferon-γ (INF-γ) production by immunocompetent cells, a pharmaceutical composition containing same, and a monoclonal antibody specific for this polypeptide. The present invention also relates to a DNA encoding the INF-γ production inducing polypeptide or peptide, methods of using the polypeptide or fragments thereof, pharmaceutical compositions, or monoclonal antibodies.

2. Description of the Related Art

Interferon-γ (INF-γ) is a protein which is known to have antiviral, antioncotic, and immunoregulatory activities, and which is produced by immunocompetent cells stimulated with antigens or mitogens. Because of these biological activities, INF-γ was expected to be used as an antitumor agent and was tested in clinical trials as a therapeutic for treating malignant tumors in general, including brain tumors. INF-γ preparations, which are now commercially available, are roughly classified into two groups, natural INF-γ polypeptides produced by immunocompetent cells and recombinant INF-γ polypeptides produced in *Escherichia coli* transformed with a DNA which encodes for natural INF-γ. In the clinical trials, either natural INF-γ polypeptide or recombinant INF-γ is administered to patients as an exogenous INF-γ.

Natural INF-γ polypeptides are usually produced by culturing established immunocompetent cells in nutrient culture media supplemented with INF-γ inducers to produce INF-γ polypeptides, and then purifying the produced INF-γ polypeptides. It is known that the type of INF-γ inducer used in the nutrient culture media greatly influences the production yield of INF-γ polypeptide as well as the ease of INF-γ purification and the safety of the final INF-γ preparations. Generally, mitogens such as concanavalin A (Con A), lentil lectin from *Lens culinaris*, pokeweed pectin from *Phytolacca americana*, endotoxin and lipopolysaccharide can be used as INF-γ inducers. However, these mitogens have problems with the molecular variety and quality of the preparation, which depend on the origin of the mitogen and purification methods used, as well as on production of mitogens with constant INF-γ inducibility in satisfactory yields. In addition, most of these mitogens induce unfavorable side effects when administered in vivo, with some even showing toxicity. As a result, it is not practical to use such mitogens to induce INF-γ production by direct in vivo administration to a patient.

Recently, some pharmaceuticals which contain as an effective ingredient a cytokine, such as interferon-α, interferon-β, TNF-α, TNF-β, interleukin 2, and interleukin 12, as well as INF-γ, were developed or are being explored for actual use. These pharmaceuticals can be used as an antitumor agent, antiviral agent, antiseptic or immunoregulatory agent and, if necessary, they can be used together with other medicaments.

Unlike chemically-synthesized pharmaceuticals, the aforesaid pharmaceuticals have the characteristic that they can be administered to patients for a relatively long period of time without inducing serious side effects. However, they also have the drawback that their therapeutic effects are relatively low, and they cannot substantially abate or cure diseases when used alone; the results vary depending on the types of diseases and symptoms to be treated. Accordingly, these pharmaceuticals are now used as a supplement to chemically-synthesized agents in the treatment of serious diseases, such as malignant tumors, to prolong the patient's life.

SUMMARY OF THE INVENTION

The present invention provides an INF-γ inducing factor which is a purified polypeptide that induces INF-γ production by immunocompetent human cells. As an embodiment of the purified factor, a purified polypeptide which induces INF-γ production by immunocompetent human cells and is obtainable from human cells is also provided.

The present invention further provides a pharmaceutical composition containing the INF-γ inducing polypeptide, where the pharmaceutical composition may advantageously include either interleukin-2 or interleukin-12.

An aspect of the present invention relates to methods of using the INF-γ inducing polypeptide. One embodiment is directed to a method for treating atopic diseases, tumors, viral diseases, bacterial diseases, or immunopathies. In particular, a method for enhancing the cytotoxicity of NK cells and method for inducing the formation of LAK cells are provided.

Also provided by the present invention is a DNA molecule encoding the INF-γ inducing polypeptide according to the present invention, a replicable recombinant DNA containing a self-replicable vector and the DNA molecule encoding the INF-γ inducing polypeptide, host cells transformed with the self-replicable vector, and a process for preparing the INF-γ inducing polypeptide.

DETAILED DESCRIPTION OF THE INVENTION

Polypeptide/Protein and Encoding DNA

Figure 1:
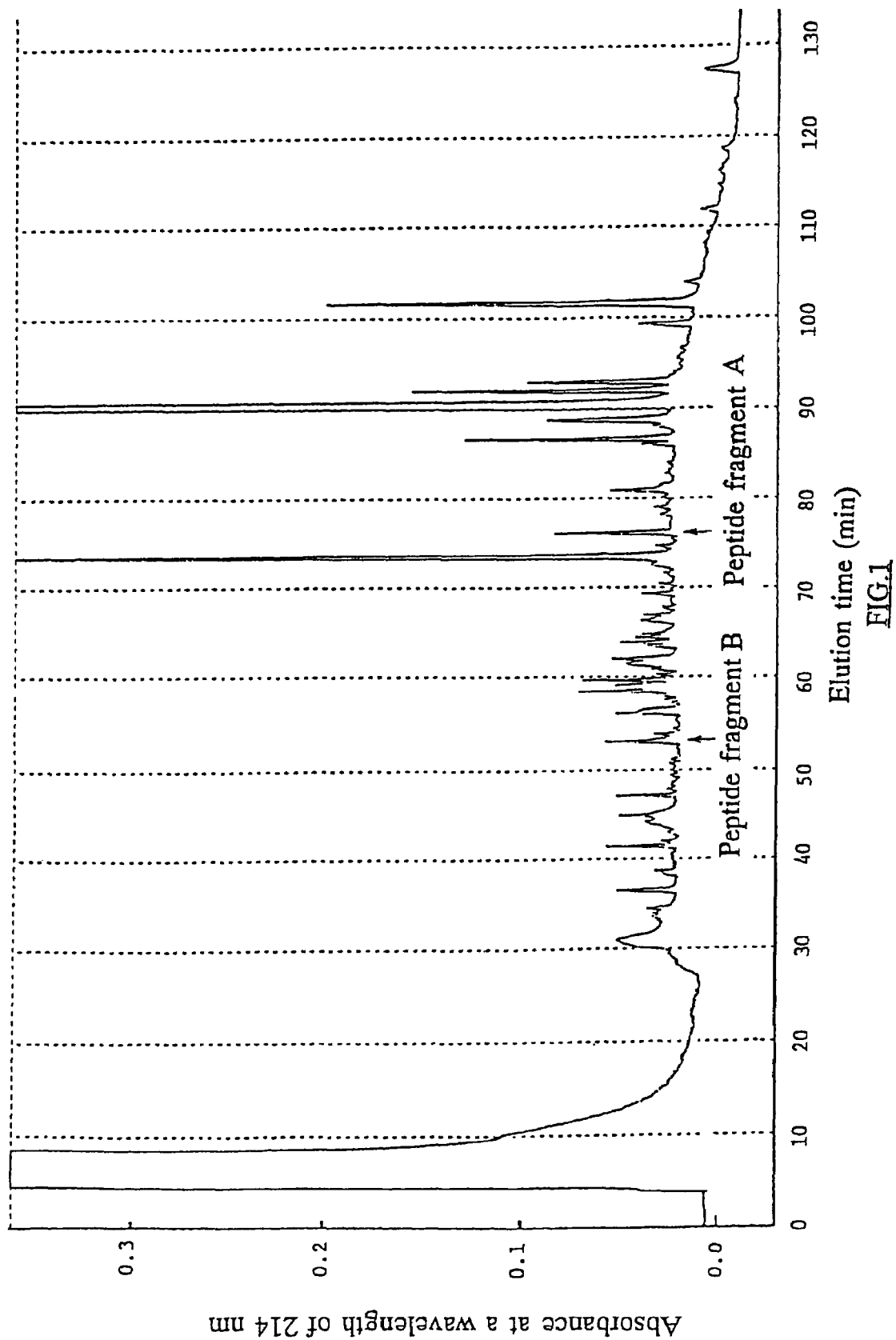
FIG. 1 is an HPLC elution pattern profile of peptide fragments obtained by trypsinizing a protein derived from mouse liver.

The present invention is based on the initial discovery of a substance in mouse liver which induces INF-γ production during studies of cytokines produced from mammalian cells in the laboratories of the present inventors. The present inventors isolated this substance by using a variety of purification methods including column chromatography as a main technique, and studied the properties and features of this substance, revealing that it is a protein with the following physicochemical properties:

(1) Molecular Weight Exhibiting a molecular weight of 19,000±5,000 daltons on sodium dodecyl polyacrylamide gel electrophoresis (SDS-PAGE);

(2) Isoelectric Point (pI) Exhibiting an isoelectric point of 4.8±1.0 on chromatofocusing;

(3) Partial Amino Acid Sequence Having the partial amino acid sequences in SEQ ID NOs: 1 and 2; and (4) Biological Activity Inducing the INF-γ production by immunocompetent cells.

This substance is a novel protein whose physicochemical properties have not been previously reported.

Based on the partial amino acid sequences obtained above, primers were chemically synthesized and used with MRNA isolated from mouse liver cells as template in a reverse transcription-polymerase chain reaction (RT-PCR) to generate DNA fragments which partially encode the protein. By using the generated DNA fragments as probes, a cDNA library prepared from MRNA was screened and it was found that the DNA of the substance isolated from mouse liver cells consists of 471 base pairs (SEQ ID NO:3) and encodes the 157 residue amino acid sequence of SEQ ID NO:4, where Xaa represents methionine or threonine.

The present inventors further studied mRNA derived from human liver cells, and found a human gene that encodes a polypeptide which induces INF-γ production by immunocompetent cells. This gene contains the nucleotide sequence of SEQ ID NO:5 and encodes a 157 amino acid residue polypeptide of SEQ ID NO:6, where Xaa represents isoleucine or threonine.

The steps and techniques used to obtain the nucleotide and amino acid sequences of SEQ ID NOs:5 and 6 are summarized below.

(1) A protein, which induces INF-γ production by immunocompetent cells, was isolated from mouse liver cells and was highly purified by combining conventional purification methods that included chromatography as a main technique.

(2) The resultant highly purified protein was digested with trypsin, and two polypeptide fragments were isolated from the resultant mixture and analyzed to determine their amino acid sequences.

(3) From mouse liver cells, mRNA was collected and used as a template in a reverse transcription-polymerase chain reaction (RT-PCR) with oligonucleotide primers (chemically synthesized based on the above partial amino acid sequences obtained from the polypeptide fragments). The DNA fragments were then screened with oligonucleotide probes which had been chemically synthesized based on partial amino acid sequences, followed by collecting a DNA fragment which partially encodes the protein.

(4) The resultant DNA fragments were labeled and hybridized with a cDNA prepared, from using mouse liver mRNA as template, followed by selection of a transformant which exhibited strong hybridization.

(5) A cDNA was isolated from the transformant, and the nucleotide sequence was determined. Comparison of the deduced amino acid sequence and the partial amino acid sequence obtained earlier revealed that the protein has the amino acid sequence of SEQ ID NO:4. In mice, the nucleotide sequence of SEQ ID NO:3 encodes this amino acid sequence of SEQ ID NO:4.

(6) A DNA fragment having the nucleotide sequence of SEQ ID NO:3 was prepared, labeled and hybridized to a cDNA library which had been prepared from mRNA derived from human liver cells as templates, followed by selecting a transformant which exhibited strong hybridization to SEQ ID NO:3.

(7) The cDNA prepared from the transformant was sequenced. The protein is a polypeptide which comprises the amino acid sequence of SEQ ID NO:6 as encoded by the nucleotide sequence of SEQ ID NO:5 in humans.

Through long term research, the present inventors have found the present polypeptide which induces INF-γ production by immunocompetent cells when allowed to act alone or together with an appropriate cofactor. As is evident from SEQ ID NO:6, this novel polypeptide, which has a molecular weight of about 18,500±3,000 on sodium dodecyl sulfate polyacrylamide gel electrophoresis (SDS-PAGE) and an isoelectric point of about 4.9±1.0 on chromatofocusing, differs from conventionally known polypeptides. The present polypeptide includes natural and recombinant polypeptides as long as they have the amino sequence of SEQ ID NO:6, where Xaa stands for isoleucine or threonine, or sequences homologous to SEQ ID NO:6. Variants, which have amino acid sequences homologous to SEQ ID NO:6, can be obtained by replacing one or more amino acid residues in SEQ ID NO:6 with different amino acid residues, by adding one or more amino acid residues to the N- and/or C-termini of SEQ ID NO:6, or by deleting one or more amino acid residues at the N- and/or C-termini of SEQ ID NO:6 without altering the inherent biological activity of the present INF-γ inducing polypeptide. Depending on the host cells into which the DNAs are introduced (even when the same DNAs are used) and on the components and the conditions of cultivation such as temperature and pH for transformant containing the DNA, variants may be generated which either lack one or more amino acid residues at the N- and/or C-termini in SEQ ID NO:6, such as fragments of SEQ ID NO:6, or contain one or more additional amino acid residues near the N-terminus of SEQ ID NO:6 through modification by internal enzymes of the host cell following DNA expression, while retaining the inherent biological properties of the polypeptide. The polypeptide is intended to encompass such variants as long as the variants induce INF-γ production by immunocompetent cells.

The present interferon-γ inducing polypeptide can be prepared by culturing transformants, which contain the encoding DNA for the polypeptide to produce the interferon-γ inducing polypeptide, and collecting the polypeptide from the resultant cultures. The transformants usable in the present invention can be obtained by, for example, introducing DNA having the nucleotide sequence of SEQ ID NO:5, sequences homologous thereto, or complementary sequences into host cells. One or more nucleotides in the nucleotide sequences can be replaced with different nucleotides by means of the degeneracy of the genetic code without altering the amino acid sequence of the present polypeptide. To express and produce the present polypeptide in host cells using such DNAs, one or more nucleotides in the nucleotide sequences which encode the present polypeptide or its variants can be replaced with different nucleotides.

Any DNA encoding the INF-γ inducing polypeptide, i.e., produced from natural sources or produced artificially, can be used in the present invention independent of their origin. Natural sources include, for example, human liver cells from which the gene containing the DNA with nucleotide sequence of SEQ ID NO:7 is obtainable. The preparation procedure is as follows: 1) fractionating to isolate poly(A)$^+$ RNA from a commercially available human liver RNA on a sucrose gradient buffer; 2) allowing a reverse transcriptase and a polymerase to act on the mRNA as a template to generate double-stranded cDNA; 3) introducing the cDNA generated into an appropriate self-replicable vector, and transforming an appropriate host such as *Escherichia coli* with the resultant recombinant DNA; 4) culturing the resultant transformant in a nutrient culture medium; and 5) collecting the proliferated transformants containing the DNA encoding the present polypeptide by the colony hybridization method. The DNA according to the present invention is obtainable by treating the transformants with conventional methods. To artificially produce the present DNA, for example, the DNA is prepared by chemical synthesis based on the nucleotide sequence of SEQ ID NO:5, or by introducing a DNA which encodes the amino acid sequence of SEQ ID NO:6 into an appropriate vector to form a recombinant DNA, introducing the recombinant DNA into an appropriate host, culturing the resultant transformant in a nutrient culture medium, isolating the proliferated transformed host cells from the culture, and collecting and recovering plasmids containing the objective DNA from the cells.

Generally, the DNA was introduced into host cells in the form of a recombinant DNA. Such a recombinant DNA usually contains the DNA and a self-replicable vector, and it can be readily prepared by recombinant DNA technology in general. Non-limiting examples of a suitable self-replicable vector are plasmid vectors such as pKK223-2, pGEX-2T, PRL-λ, pBTrp2 DNA, pUB110, Yep13, Ti plasmid, Ri plasmid and pBI121. From among these vectors, pKK223-2, pGEX-2T, PRL-λ, pBTrp2 DNA, pUB110 and YEp13 are suitably used when the present DNA is to be transformed into and expressed in yeast and procaryotes such as microorganisms of the species *Escherichia coli* and *Bacillus subtilis*, whereas Ti plasmid, Ri plasmid and pBI121 are suitably used when transformation and expression in animal and plant cells is desired.

To incorporate the present DNA into these vectors, conventional methods used in the field can be arbitrarily used: genes containing the present DNA and self-replicable vectors are cleaved with restriction enzymes and/or ultrasonic treatment, and the resultant DNA fragments and vector fragments are ligated. To cleave genes and vectors, restriction enzymes, which specifically act on nucleotide sequences, more particularly those type II restriction enzymes such as Sau3AI, EcoRI, HindIII, BamHI, SalI, XbaI, SacI and PstI, are used to facilitate the ligation of DNA fragments and vector fragments. To ligate the DNA fragments and vector fragments, the fragments to be ligated are first annealed, if necessary, and then treated with a DNA ligase in vivo or in vitro. The recombinant DNAs thus obtained can be readily introduced into appropriate host cells, and this would enable the unlimited replication of the DNAs through the culturing of transformed host cells.

The recombinant DNAs usable in the present invention can be introduced into appropriate host cells such as cells of yeasts and microorganisms of the species *Escherichia coli* and *Bacillus subtilis*. When microorganisms of *Escherichia coli* are used as host cells, they are cultured in the presence of the recombinant DNAs and calcium ions, and when microorganisms of the species *Bacillus subtilis* are used as host cells, the competent cell method and the protoplast method are used for obtaining transformants. In order to obtain the desired transformant clone, transformants are screened/selected by the colony hybridization method or by culturing all the transformants in nutrient culture media, and screening/selecting those which produce polypeptides capable of inducing INF-γ production by immunocompetent cells.

The transformants thus obtained produce the present polypeptide intracellularly or extracellularly when cultured in nutrient culture media. Non-limiting examples of such nutrient culture media are liquid culture media which contain carbon sources, nitrogen sources and minerals, as well as amino acids and/or vitamins as a micronutrient. The carbon sources usable in the present invention include saccharides such as starch, starch hydrolysates, glucose, fructose and sucrose. The nitrogen sources usable in the present invention include nitrogen-containing organic and inorganic compounds such as ammonia and their salts, urea, nitrates, peptone, yeast extract, defatted soy bean, corn steep liquor, beef extract, etc.

Transformants are inoculated into nutrient culture media and incubated at a temperature of 25-65° C. and at a pH of 5-8 for about 1-10 days under aerobic conditions by the agitation-aeration method, etc., to obtain cultures containing the present polypeptide. Although the cultures can be used intact as an INF-γ inducer, they are subjected, if necessary, to ultrasonication and/or cell lysis enzymes in order to disrupt cells, followed by filtering or centrifuging the resultant suspensions to remove intact cells and cell debris, and further by purifying the resultant supernatants containing the present polypeptide. The purification methods usable in the present invention are, for example, those which are generally used in this field to purify biologically active substances, i.e., concentration, salting out, dialysis, separatory sedimentation, gel filtration chromatography, gel electrophoresis, and isoelectrophoresis, and, if necessary, two or more of the purification methods can be used in combination. The resultant purified solutions containing the present polypeptide can be concentrated and/or lyophilized into liquids or solids suitable to meet the final use of the polypeptide.

The polypeptide of the present invention can also be isolated from human cells as a protein. The term "polypeptide" as used herein for the human INF-γ inducing polypeptide is intended to mean polypeptides and glycoproteins in general which induce INF-γ production by immunocompetent cells and contain the amino acid sequence of SEQ ID NO:14. Depending on the type and conditions of propagating human cells, the polypeptide has the amino acid sequences of SEQ ID NOs:14 and 15 at the N- or C-terminal region, respectively, and occasionally has the amino acid sequence of SEQ ID NO:6 (where Xaa represents isoleucine or threonine) as a complete amino acid sequence, including the amino acid sequences of SEQ ID NOs:16 and 17 as an internal fragment. When subjected to peptide mapping using clostripain, peptide fragments of SEQ ID NOs:15, 16, 17 and 19 were observed. The polypeptide is detected as a protein band corresponding to a molecular weight of 14,000-24,000 daltons (usually 18,000-19,500 daltons) when determined on SDS-PAGE in the presence of a reducing agent such as dithiothreitol. Depending on the type and conditions of propagating human cells, one or more amino acid residues may be added to the N- and/or C-termini (SEQ ID NOs:14 and 15) or one or more amino acid residues at the N- or C-termini may be deleted. Any INF-γ inducing polypeptide can be used in the present invention as long as it is derived from a human cell, and has either of these amino acid sequences and the activity of inducing INF-γ production when acting on immunocompetent cells alone or together with an appropriate cofactor.

These INF-γ inducing polypeptides according to the present invention can be produced by the present process using human cells. Usually, the human cells used in the present invention include cell lines derived from human hematopoietic cells such as lymphoblasts, lymphocytes, monoblasts, monocytes, myeloblasts, myelocytes, granulocytes and macrophages. Non-limiting examples of these cell lines are lymphomas and leukemias such as myelocytic leukemia, promyelocytic leukemia, adult T-cell leukemia, and hairy cell leukemia, and more specifically, HBL-38 cell, HL-60 cell (ATCC CCL240), K-562 cell (ATCC CCL243), KG-1 cell (ATCC CCL246), Mo cell (ATCC CRL8066), THP-1 cell (ATCC TIB202), U-937 cell (ATCC CRL1593) as reported by Jun MINOWADA in *Cancer Review*, 10:1-18 (1988), and A-253 cell (ATCC HTB41), which is an epidermoid carcinoma of the human submaxillary gland. Mutants of these cell lines can also be used in the present invention. Because these cell lines readily proliferate and produce large quantities of the present polypeptide, they can be advantageously used in the present invention. In particular, epidermoid carcinoma cell lines such as A-253, and human myelomonocytic cell lines such as HBL-38, HL-60, KG-1, THP-1, and U-937 cells have extremely high productivity for the present polypeptide and are most suitable for use in the present invention.

In the present process, the above-mentioned human cells are first allowed to propagate, with the present polypeptide then being collected from the propagated cells. The method used to propagate these human cells according to the present invention is not specifically limited, and any conventional in vivo or in vitro propagation method can be used. The in vitro propagation method is intended to mean a method for propagating cells using nutrient culture media, which comprises suspending human cells in RPMI 1640 medium, MEM medium and DMEM medium, which are conventionally used in the art for propagating animal cells, supplemented with 0.3-30 w/v % of fetal bovine serum to give a cell density of about $1 \times 10^5$-$1 \times 10^6$ cells/ml, and culturing these cells at a temperature of 36-38° C., preferably at a temperature of about 37° C. and at a pH of 7-8, more preferably at a pH of 7.2-7.4, for about 1-7 days where the culture media are replaced with fresh culture media. Afterwards, the propagated cells were separated from the culture to obtain the objective polypeptide. Depending on the type and conditions for culturing human cells, some cells can excrete the present polypeptide extracellularly while being cultured. When inducers, such as mitogens and/or INF-γs which induce the production of the present polypeptide by human cells are present in the culture media, most or all of the polypeptide is produced extracellularly. In this case, the polypeptide can be collected from the culture supernatant.

The method for in vivo propagation of human cells in warm-blooded animals other than humans includes injecting antithymocyte antibodies derived from rabbits into rodents, such as newborn mice, nude mice, rats, nude rats, guinea pigs, and hamsters, to suppress immunoreaction in the animals, injecting subcutaneously or intraperitoneally about $1 \times 10^5$-$1 \times 10^8$ of human cells per animal into the animals or placing the human cells in diffusion chambers embedded within or outside of the body of the animals while allowing the body fluid of the animals to circulate in the chambers, and feeding the animals by conventional methods for about 2-10 weeks. During the feeding, the human cells propagate in the presence of body fluid from the animals. The propagated human cells are collected in the form of a tumor mass, ascites or cell suspension. If necessary, the objective polypeptide is collected after suspending and washing these human cells with an appropriate solvent. The in vivo propagation method has an advantage over the in vitro propagation method in that the desired cells can be obtained in a shorter period of time, at a lower labor cost and in a sufficiently high yield. The in vivo propagation method is disclosed, for example, in Japanese Patent Publication No. 54,158/81.

To collect and recover the present polypeptide from the propagated cells, these cells are disrupted by ultrasonic energy before or after separation from the culture, homogenizing, freezing and thawing, or by soaking these cells in low osmotic solvents, and then collecting the polypeptide from the resulting cell debris or from a mixture of cell debris and culture supernatant. To collect the present polypeptide from the cell debris or the mixture, the cell debris or the mixture can be subjected directly, or after incubation at about 37° C. for 1-24 hours, to the following conventional methods for purifying biologically active substances in the art: salting out, dialysis, filtration, concentration, separatory sedimentation, gel filtration chromatography, ion-exchange chromatography, hydrophobic chromatography, adsorption chromatography, affinity chromatography, chromatofocusing, gel electrophoresis and/or isoelectrophoresis. Two or more of these conventional methods can be selectively used in combination. The collected polypeptide can be concentrated and/or lyophilized into a liquid or solid form for its intended final use. The monoclonal antibody according to the present invention, as discussed below, is advantageously used to purify the present polypeptide. Immunoaffinity chromatography using the monoclonal antibody yields the highest possible purity of the present polypeptide at the lowest cost and effort.

Agent, Pharmaceutical Compositions and Methods of Use

As described in the preceding section, the polypeptide as an agent according to the present invention has a property of inducing stable INF-γ production by immunocompetent cells. INF-γs are well-known to contribute to human biophylaxis through their protection against infectious bacteria, their growth inhibitory activity on malignant tumors, their immunoregulatory activity, and their inhibitory activity on the production of immunoglobulin E antibody.

In *Cytokines in Cancer Therapy*, edited by Frances R. Balkwill, translated by Yoshihiko WATANABE (1991), published by Tokyo-Kagaku-Dojin, Tokyo, Japan, it is reported that almost satisfactory results were obtained when a treatment, using killer cells such as natural killer (NK) cells and lymphokine-activated killer (LAK) cells, was applied on a variety of human diseases including antitumor immunotherapy. Recently, it has been noted that there is a relationship between the therapeutic effect and the induction of killer cells or the enhancement of the cytotoxicity by killer cells using cytokines. For example, T. FUJIOKA reported in *British Journal of Urology*, 73 (1): 23-31 (1994), that in antitumor immunotherapy using LAK cells and interleukin 2, interleukin 2 strongly induced LAK cell formation and exerted a remarkable cancer metastasis-inhibitory activity on human cancers without causing serious side effects. Thus, it is shown that INF-γ and killer cells are closely involved in the treatment and/or prevention of a variety of human diseases, and greatly contribute to their treatment or remission.

When administered to humans, the present agent induces INF-γ production by immunocompetent cells in vivo, and exerts a satisfactory therapeutic and/or prophylactic effect on diseases susceptible to treatment with INF-γ, including viral diseases such as AIDS and condyloma acuminatum; malignant tumors such as malignant nephroma, granuloma, mycosis fungoides, and brain tumor; and immunopathies such as articular rheumatism and allergy. The use of this agent according to the present invention is not restricted to only humans, but can include other mammals such as mouse, rat, hamster, dog, cat, cow, horse, goat, sheep, pig, and monkey.

Because the present polypeptide induces INF-γ production by human immunocompetent cells, agents for diseases susceptible to treatment with INF-γ and containing the polypeptide as an effective ingredient stimulate human immunocompetent cells to produce INF-γ by administering the polypeptide to humans, and exert a positive effect on the treatment and/or prevention of INF-γ susceptive diseases. The polypeptide having the amino acid sequence of SEQ ID NO:6 has the properties of enhancing the cytotoxicity of killer cells, i.e., NK cells, LAK cells, cytotoxic T-cells, and inducing INF-γ production by immunocompetent cells without causing serious side effects. Killer cells participate in the treatment and/or the prevention of diseases susceptible to treatment with INF-γ when the present polypeptide is used to induce INF-γ production by immunocompetent cells in vivo, to enhance the cytotoxicity of killer cells such as cytotoxic T-cells and NK- and LAK-cells, and to induce the formation of killer cells similar to the polypeptides described in the later described Examples. When the INF-γ inducing polypeptide augments the cytotoxicity of killer cells or induces the formation of killer cells, it exerts a strong effect in treating inveterate diseases such as malignant tumors. It can also be used together with interleukin 2 and/or tumor necrosis factor to improve the therapeutic effect and reduce the side effects in treatments using adoptive immunity for malignant tumors including solid tumors such as lung cancer, renal cancer, and breast cancer.

Because the present polypeptide has a strong INF-γ production inducibility and has relatively low toxicity, it can induce a desired level (amount) of INF-γ production in a small amount. The present polypeptide does not cause serious side effects even when administered to patients at a relatively high dose because it has low toxicity. Therefore, the present polypeptide is advantageous in that it quickly induces a desired level of INF-γ production without strictly controlling the dose. The present polypeptide, when of human cell origin, is particularly advantageous in that it causes less side effects and induces less antibodies when administered to humans in the form of a pharmaceutical composition as compared with polypeptides produced artificially by recombinant DNA techniques.

The term "diseases susceptible to treatment with INF-γ" as used herein means diseases in general which can be directly or indirectly treated and/or prevented by INF-γ and/or killer cells. For example, viral diseases such as hepatitis, herpes syndrome, condyloma acuminatum, and AIDS; infectious diseases such as *candidiasis, malaria, cryptococcosis,* and *Yersinia*; malignant solid tumors such as renal cancer, mycosis fungoides, and chronic granulomatous disease; hematopoietic malignant tumors such as adult T-cell leukemia, chronic myelocytic leukemia, and malignant leukemia; and immunopathies/immune diseases such as allergy and rheumatism. When used with interleukin 3, the present polypeptide exerts a strong effect on the treatment or the remission of leukopenia and thrombocytopenia induced by radio- and chemotherapies for treating leukemia, myeloma, and malignant tumors.

The present agent for susceptive diseases can be widely used in the treatment and/or the prevention of the above diseases as an antitumor agent, antiviral agent, antiseptic, immunotherapeutic agent, platelet-increasing agent, or leukocyte-increasing agent. Depending on the type of agents and the symptom of diseases to be treated, the present agent is generally processed into a liquid, paste or solid form which contains 0.000001-100 w/w %, preferably 0.0001-0.1 w/w % of the present polypeptide, on a dry solid basis (d.s.b.).

The present agent can be used intact or processed into compositions by mixing with physiologically-acceptable carriers, adjuvants, excipients, diluents and/or stabilizers, and, if necessary, further mixing with one or more biologically-active substances such as interferon-α, interferon-β, interleukin 2, interleukin 3, interleukin 12, TNF-α, TNF-β, carboquone, cyclophosphamide, aclarubicin, thiotepa, busulfan, ancitabine, cytarabine, 5-fluorouracil, 5-fluoro-1-(tetrahydro-2-furyl) uracil, methotrexate, actinomycin D, chromomycin $A_3$, daunorubicin, doxorubicin, bleomycin, mitomycin C, vincristine, vinblastine, L-asparaginase, radio gold colloidal, Krestin®, picibanil, lentinan, and Maruyama vaccine. Among these combinations, a combination of the present polypeptide and interleukin 2 is especially useful because interleukin 2 acts as a cofactor for the present polypeptide when the present polypeptide induces IFN-γ production by immunocompetent cells. The combination of the present polypeptide and a natural or recombinant human interleukin 2 induces a relatively high level of INF-γ production using only a small amount of the present polypeptide, which by itself does not substantially induce INF-γ production by immunocompetent cells. A combination of the present polypeptide and interleukin 12 also induces a greater level of INF-γ production than could be readily attained by the present polypeptide alone. Because the present polypeptide increases the inhibitory activity of interleukin 12 on the production of immunoglobulin E antibody in the human body, the present polypeptide can be advantageously used to treat immunopathies such as atopic diseases including atopic asthma, atopic bronchial asthma, hay fever, allergic rhinitis, atopic dermatitis, angioedema, and atopic disorders of the digestive system. The sole administration of the present polypeptide to humans can attain the desired therapeutic effect because interleukin 12 is inherently present in small amounts in the human body.

The form of the present agent for diseases susceptible to treatment with INF-γ includes those in a unit dose form, which are physically formulated medicaments suitable for administration and contain the present polypeptide in a daily dose or in a dose from ¼₀ to several times (i.e., up to 4 time) the daily dose. Examples of these medicaments are injections, liquids, powders, granules, tablets, capsules, sublinguals, opthalmic solutions, nasal drops, and suppositories.

The present agent can be orally or parenterally administered to patients, and as described below, it can be used to activate antitumor cells in vitro. In both administrations, the agent exerts a satisfactory effect in the treatment and/or the prevention of diseases susceptible to treatment with INF-γ. Although it varies depending on the types of diseases susceptible to treatment with INF-γ and the symptoms of patients before and after administration, the agent can be orally administered to patients or parenterally administered to the intradermal tissues, subcutaneous tissues, muscles, and veins of patients at a dose of about 0.1 μg to 50 mg per shot, preferably about 1 μg to 1 mg per shot, 1-4 times/day or 1-5 times/week, for one day to one year.

The present agent can be also used in a so-called "antitumor immunotherapy" using interleukin 2. Generally, antitumor immunotherapy is roughly classified into (i) a method for directly administering interleukin 2 to patients with malignant tumors, and (ii) a method for introducing cells which were previously activated in vitro by interleukin 2, i.e., adoptive immunotherapy. The immunotherapeutic effect can be significantly enhanced when the present polypeptide is administered in combination with interleukin 2. In method (i), the present polypeptide is administered to patients in an amount of about 0.1 μg/shot/adult to 1 mg/shot/adult either for 1-10 times before the administration of interleukin 2 or simultaneously with interleukin 2. The dose of interleukin 2 is generally about 10,000-1,000,000 units/shot/adult, although it varies depending on the types of malignant tumors, patients' symptoms, and the dose of the present polypeptide. In method (ii), mononuclear cells and lymphocytes collected from patients with malignant tumors are cultured in the presence of interleukin 2 and about 0.1 ng to 1 μg of the polypeptide per $1 \times 10^6$ blood cells. After culturing for a prescribed period of time, NK or LAK cells were collected from the culture and introduced back into the same patient. Diseases which can be treated by the present antitumor immunotherapy are, for example, hematopoietic malignant tumors such as leukemia and malignant lymphoma, solid malignant tumors such as colonic cancer, rectal cancer, large intestinal cancer, gastric cancer, thyroid carcinoma, cancer of the tongue, bladder carcinoma, choriocarcinoma, hepatoma, prostatic cancer, carcinoma uteri, laryngeal, lung cancer, breast cancer, malignant melanoma, Kaposi's sarcoma, cerebral tumor, neuroblastoma, tumor of the ovary, testicular tumor, osteosarcoma, cancer of the pancreas, renal cancer, hypernephroma, and hemangioendothelioma.

The present polypeptide can also be used as an inducer for INF-γ production by cell culture methods and is usually added to nutrient culture media for INF-γ production in cultured immunocompetent cells. Leukocytes separated from mammalian peripheral blood or established cell lines of immunocompetent cells such as HBL-38 cell, Mo cell (ATCC CRL8066), Jurkat cell (ATCC CRL8163), HUT78 cell (ATCC TIB161), EL4 cell (ATCC TIB39), L-12-R4 cells, and mutants thereof are suspended in culture media containing about 0.1-1,000 ng/ml of the present polypeptide, preferably about 1-100 ng/ml of the present polypeptide. If necessary, these cells are cultured in nutrient culture media supplemented with T-cell stimulants such as mitogens, interleukin 2, and anti-CD3 antibody for about 1-100 hours and the cells and cultured at a temperature of about 30-40E$\underline{C}$ and a pH of about 5-8 while replacing the culture media with fresh media. From the resulting cultures, the present polypeptide can be collected by one or more conventional methods such as salting out, dialysis, filtration, concentration, separatory sedimentation, gel filtration chromatography, ion-exchange chromatography, hydrophobic chromatography, adsorption chromatography, affinity chromatography, chromatofocusing, gel electrophoresis and isoelectrophoresis.

Monoclonal Antibodies and Uses Thereof

As described above, the present polypeptide has a property of inducing INF-γ production by immunocompetent cells, and is expected to be used in a variety of fields as an INF-γ inducer, antiviral agent, antitumor agent, antibacterial agent, immunoregulatory agent, and blood platelet enhancing agent. In general, the development of methods for efficiently purifying biologically active polypeptides to relatively high purity and for assaying many samples in parallel are needed when the polypeptides are to be incorporated into pharmaceuticals. Although the best material for enabling purification of and assay for the present polypeptide is a monoclonal antibody, no such monoclonal antibody specific for the present polypeptide has been previously established before the present invention.

The monoclonal antibody according to the present invention includes monoclonal antibodies in general which are specific for the present polypeptide having the amino acid sequence of SEQ ID NO:6 or of a sequence homologous to SEQ ID NO:6, regardless of its source, origin or class. The homologous amino acid sequence includes those which are obtained by replacing one or more amino acid residues in SEQ ID NO:6 with different amino acid residues, by adding one or more amino acid residues to the N- and/or C-termini or by deleting one or more amino acid residues from the N- and/or C-termini, while substantially not losing the activity of inducing the INF-γ production by immunocompetent cells.

The monoclonal antibody according to the present invention can be obtained by using the present polypeptide or its antigenic fragments. For example, the antibody can be obtained by preparing hybridomas using mammalian cells capable of infinite proliferation and antibody-producing cells collected from mammals immunized with the fragments, selecting clones of hybridomas capable of producing the monoclonal antibody, and culturing the clones in vivo or in vitro.

The present polypeptide as an antigen can be obtained by culturing transformants into which a DNA encoding the amino acid sequence of SEQ ID NO:6 or a homologous nucleotide sequence was introduced. Generally, the present polypeptide is used intact or in a partially purified form. The antigenic fragments can be prepared by chemically or enzymatically hydrolyzing the wholly purified or partially purified present polypeptide, or they can be synthesized by peptide synthesis based on the amino acid sequence of SEQ ID NO:6.

The immunization method that can be used in the present invention includes conventional methods used in the art. For example, antigens alone or in combination with adequate adjuvants are injected into mammals intravenously, intradermally, subcutaneously or intraperitoneally, and they are fed for a prescribed period. Any mammal can be used in the present invention without special restriction as long as the desired antibody-producing cells can be obtained regardless of the animal's species, weight and sex. In general, rodents such as rats, mice and hamsters are used, and the most suitable animal is selected from these rodents while also evaluating compatibility for producing hybridomas with the above mammalian cells capable of infinite proliferation.

Depending on the species and weight of animal used, the total dose of antigen is generally in the range of about 5-500 μg per animal and is administered 2-5 times at an interval of 1-2 weeks. At 3-5 days after the final administration, the animal's spleen is extracted and dispersed into a suspension of spleen cells (antibody-producing cells).

The antibody-producing spleen cells and the mammalian cells capable of infinite proliferation are fused to form a cell fusion mixture containing the desired hybridomas. Mammalian cells capable of infinite proliferation include cell strains from mouse myeloma such as P3-NS1-Ag4-1 cells (ATCC TIB18), P3-x63-Ag8 cells (ATCC TIB9), SP2/0-Ag14 cells (ATCC CRL1581), and mutants thereof. Cell fusion methods that can be used in the present invention include conventional methods using an electric pulse and a cell fusion accelerator such as polyethylene glycol and sendai virus (HVJ). For example, antibody-producing cells and mammalian cells are suspended in fusion media containing fusion accelerators in a ratio of about 1:1 to 1:10, and incubated at about 30-40° C. for about 1-5 min. Conventional media such as minimum essential medium (MEM), RPMI 1640 medium, and Iscove's Modified Dulbecco's Medium (IMDM) are preferably used as a fusion medium without the addition of serums such as calf serum.

To select the desired hybridomas, the resultant cell fusion mixture was transferred to a selection media such as HAT medium, and incubated at about 30-40° C. for about 3 days to 3 weeks to kill cells that were not hybridomas. Hybridomas were then cultured in the usual manner, and the antibodies secreted by the hybridomas into the culture media were assayed for reactivity with the present polypeptide. Examples of such an assay are conventional assays for detecting antibodies, such as enzyme immunoassay, radioimmunoassay, and bioassay. *Tan-Clone-Kotai-Jikken-Manual (Experimental Manual for Monoclonal Antibody)*, edited by Sakuji TOYAMA and Tamie ANDO, published by Kodansha Scientific, Ltd., Tokyo, Japan, pp. 105-152 (1991) describes a variety of suitable assays. Hybridomas which produce antibodies that are specific to the present polypeptide are readily cloned by using limiting dilution to obtain the hybridoma according to the present invention.

The monoclonal antibody according to the present invention can be obtained by culturing the hybridoma in vivo, i.e., in animals, or in vitro. Conventional methods for culturing mammalian cells can be used. In the case of in vivo culture, the monoclonal antibody is collected from the animals' ascites and blood. Examples of such methods include salting out, dialysis, filtration, concentration, centrifugation, separatory sedimentation gel filtration chromatography, affinity chromatography, high-performance liquid chromatography (HPLC), gel electrophroesis, and isoelectrophoresis, and, if necessary, two or more of these techniques can be used in combination. The resultant purified monoclonal antibodies can be concentrated or dried into products in the form of a liquid or a solid depending on their final use.

The present monoclonal antibody is extremely useful for purifying the present polypeptide by immunoaffinity chromatography. Such a purification technique includes contacting the monoclonal antibody with a mixture containing the present polypeptide and impurities such as proteins other than the desired polypeptide so as to adsorb the present polypeptide on the antibody, and then subsequently desorbing the present polypeptide from the antibody after the impurities are removed. These steps are generally carried out in an aqueous system. The monoclonal antibody is generally used in an immobilized form on gel water-insoluble carriers which are packed in cylindrical columns. Cultures of transformants or their partially purified products are fed to the columns to substantially adsorb the present polypeptide to the immobilized monoclonal antibody. The present polypeptide is then readily desorbed from the antibody by altering the pH around the antibody. For example, in the case of using a monoclonal antibody of the IgG class, the adsorbed polypeptide is desorbed and eluted from the columns at an acidic pH, usually at a pH of 2-3, whereas in the case of a monoclonal antibody of the IgM class, the present polypeptide is desorbed and eluted from the columns at an alkaline pH, usually at a pH of 10-11. The purification method according to the present invention attains a relatively high level purification of the present polypeptide with only the minimum of labor cost and time. As described above, the present monoclonal antibody specifically reacts with the present polypeptide which induces INF-γ production by immunocompetent cells. Therefore, the monoclonal antibody is widely used in the purification and detection of the present polypeptide and can be prepared in a desired amount by a preparation using hybridomas.

The monoclonal antibody according to the present invention has relatively wide applicability to a variety of fields in which the detection of the present polypeptide is advantageous. When used in labelled immunoassays such as radioimmunoassay, enzyme immunoassay, and fluorescent immunoassay, the monoclonal antibody can qualitatively and quantitatively detect the present polypeptide in samples instantly and accurately. In such assays, the monoclonal antibody is labelled, for example, with radioisotopes, enzymes and/or fluorescent substances prior to use. The antibody specifically reacts with the present polypeptide to exhibit an immunoreaction, and accurately detects a slight amount of the present polypeptide in samples by measuring the level of immunoreaction for these labelled substances. As compared with bioassay, labelled immunoassay can assay many samples in parallel, reduce the assay time and labor cost, and provide data with relatively high accuracy. Thus, the present detection method is useful for controlling the production steps of the present polypeptide and for quality control of the final products. The techniques for labelling monoclonal antibody or for the labelling assay are not described in detail because the present invention does not in itself relate to such labelling techniques. These techniques are however described in detail in "*Enzyme Immunoassay*", edited by P. Tijssen, translated by Eiji ISHIKAWA, published by Tokyo-Kagaku-Dojin, pp. 196-348 (1989).

Having now generally described the present invention, the same will be more readily understood through reference to the following examples, which are provided by way of illustration and is not intended to be limiting of the present invention. The techniques used herein are conventionally known in the art. For example, conventional molecular genetic techniques are disclosed in Sambrook et al., *Molecular Cloning: A Laboratory Manual*, second edition, Cold Spring Harbor Laboratory Press, Cold Spring Harbor, N.Y., 1989, and in Muramatsu, M., *Laboratory Manual for Genetic Engineering*, Maruzen Co., Ltd., Tokyo, Japan, 1988.

EXAMPLES

Example 1

Preparation of Purified Polypeptide 600 female 8 week old CD-1 mice were each injected intraperitoneally with 1 mg of dead *Corynebacterium parvum* (ATCC 11827) which had been preheated at 60° C. for 1 hour, and the mice were fed in the usual manner for 7 days and then each was injected intravenously with 1 μg of a purified lipopolysaccharide derived from *Escherichia coli*. At 1-2 hours after the intravenous injection, the mice were sacrificed by drawing to collect their blood, followed by removal of their livers, disruption of the livers with a homogenizer in an 8-fold volume of 50 mM phosphate buffer (pH 7.3), and extraction of the resultant suspension. The resultant extract was centrifuged at about 8,000 rpm for 20 min, and approximately 9 L of the supernatant was admixed with saturated ammonium sulfate in 50 mM phosphate buffer (pH 7.3) to give a saturation degree of 45 w/v %. The resultant solution was allowed to stand at 4° C. for 18 hours and centrifuged at about 8,000 rpm for 30 min to obtain about 19 L of supernatant containing the present polypeptide.

The supernatant was fed to a column packed with about 4.6 L of PHENYL SEPHAROSE, a product of Pharmacia LKB Biotechnology AB, Uppsala, Sweden, which had been equilibrated with 50 mM phosphate buffer (pH 7.3) containing 1 M ammonium sulfate. The column was washed with a fresh preparation of the same buffer, and fed at an SV (space velocity) of 0.57 with a linear gradient buffer ranging from 1 M to 0.2 M ammonium sulfate in 50 mM phosphate buffer (pH 7.3). Fractions containing the present polypeptide eluted at 0.8 M ammonium sulfate and were collected and pooled into a volume of about 4.8 L which was then concentrated with a membrane filter, dialyzed against 20 mM phosphate buffer (pH 6.5) at 4° C. for 18 hours, and fed to a column packed with about 250 ml of DEAE-SEPHAROSE, a product of Pharmacia LKB Biotechnology AB, Uppsala, Sweden. The column was washed with a fresh preparation of the same buffer and fed at an SV of 1.2 with a linear gradient buffer ranging from 0 to 0.2 M sodium chloride in 20 mM phosphate buffer (pH 6.5) to elute and collect approximately 260 ml fractions containing the present polypeptide eluted at a concentration of about 0.13 M sodium chloride.

Fractions containing the present polypeptide were collected, pooled, concentrated and dialyzed against 25 mM Bis-Tris buffer (pH 7.1) at 4° C. for 18 hours. The dialyzed solution was applied to a column packed with about 24 ml of MONO-P, a product of Pharmacia LKB Biotechnology AB, Uppsala, Sweden, and eluted with 10 v/v % polybuffer 74 (pH 4.0) while decreasing the pH from 7 to 4 to obtain approximately 23 ml of an eluate (pH of about 4.8) containing the present polypeptide. The eluate was concentrated, fed to a column packed with SUPERDEX 75, a product of Pharmacia LKB Biotechnology AB, Uppsala, Sweden, which had been equilibrated with 7 mM phosphate buffer (pH 7.2), 3 mM sodium dihydrogen phosphate, and 139 mM sodium chloride, and subjected to gel filtration chromatography to elute fractions containing the present polypeptide of about 19,000 daltons with a fresh preparation of the same buffer. The fractions were pooled and concentrated for use in Example 2. The yield of the present polypeptide was about 0.6 μg/mouse.

Example 2

Partial Amino Acid Sequence

A portion of an aqueous solution containing the purified polypeptide in Example 1 was concentrated to a volume of about 50 μl and then admixed with 25 μl of a solution containing 3 w/v % SDS, 60 v/v % glycerol, and 60 mg/ml dithiothreitol. The resultant mixture was incubated at 50° C. for 30 min, loaded onto 15 w/v % polyacrylamide gel, and electrophoresed in the usual manner. The resultant gel was stained by soaking it in a mixture solution of 10 v/v % aqueous acetic acid solution and 50 v/v % aqueous methanol containing 0.1 w/v % Coomassie brilliant blue R 250, destained by repeatedly washing the gel with a mixture solution of 12 v/v % aqueous methanol and 7 v/v % aqueous acetic acid solution, and then washed by soaking it in distilled water for 18 hours. A portion of the gel, which was stained with Coomassie brilliant blue and contained the present polypeptide, was cut out of the gel and lyophilized.

The lyophilized gel was soaked in a 0.6 ml 100 mM sodium hydrogen carbonate solution containing 2 μg/ml TPCK TRYPSIN, 0.5 mM calcium chloride, and 0.02 v/v % aqueous TWEEN 20, followed by incubation at 37° C. for 18 hours to trypsinize the protein. The resultant mixture was centrifuged to obtain a supernatant, and the resultant precipitate was soaked in 1 ml of 1 v/v % aqueous trifluoroacetate containing 0.001 v/v % TWEEN 20, shaken for 4 hours at ambient temperature, and centrifuged to obtain a supernatant. The newly formed precipitate was successively treated similarly as above with 70 v/v % aqueous trifluoroacetate containing 0.001 v/v % TWEEN 20 and with 50 v/v % aqueous acetonitrile to obtain a supernatant. The resultant supernatant and the previously obtained supernatant were pooled and concentrated to give 250 μl which was then centrifugally filtered.

The resultant peptide fragment-containing aqueous solution was fed to an HPLC ODS-120T column (HPLC column commercialized by Tosoh Corporation, Tokyo, Japan), which had been previously equilibrated with 0.1 v/v % aqueous trifluoroacetate, and the column was washed with 0.1 v/v % aqueous trifluoroacetate, and then fed with 0.1 v/v % trifluoro acetate at a flow rate of 0.5 ml/min while increasing the concentration of aqueous acetonitrile from 0 to 70 v/v %. The concentration of peptides in the eluate was monitored by a spectrophotometer at wavelengths of 214 nm and 280 nm. Fractions eluted at approximately 75 min and 55 min after initiating the elution were collected and respectively designated peptide fragment A and peptide fragment B. The elution pattern is shown in FIG. 1.

Peptide fragments A and B were analyzed on a model 473 A protein sequencer commercialized by Perkin-Elmer Corp., Instrument Division, Norwalk, Conn., and revealed to have the amino acid sequences of SEQ ID NOs:1 and 2.

Example 3

Nucleotide Sequence of CDNA Encoding Polypeptide and Amino Acid Sequence of Encoded Polypeptide 3-1: Preparation of Whole RNA Three grams of wet mouse liver cells, prepared similarly as in the method of Example 1, was weighed, soaked in 20 ml of a solution containing 6 M guanidine isothiocyanate, 10 mM sodium citrate, and 0.5 w/v SDS, and disrupted with a homogenizer. Thirty-five ml centrifugation tubes, into which 25 ml of 0.1 M EDTA (pH 7.5) containing 5.7 M cesium chloride was poured, and 10 ml of the homogenized cell suspension was overlaid on top of the EDTA-cesium chloride solution in the tubes, were prepared. The tubes were centrifuged at 25,000 rpm at 20°, for 20 hours to collect RNA fractions, and the fractions were pooled, distributed into 15-ml centrifugation tubes, and mixed with equal volumes of a mixture of chloroform and 1-butanol (4:1 by volume). The tubes were vibrated/vortexed for 5 min and centrifuged at 4° C. and at 10,000 rpm for 10 min, and the resulting aqueous phase layers were collected, pooled, and mixed with a 2.5 volumes of ethanol, and allowed to stand at −20° C. for 2 hours to precipitate whole RNA. The precipitate was collected, pooled, washed with 75 v/v % aqueous ethanol, and dissolved in 0.5 ml of sterilized distilled water for use in Example 3-2 below. The yield of RNA was about 4 mg, on a dry solid basis (d.s.b.).

3-2: Preparation of cDNA Fragments Encoding Partially the Present Polypeptide

One μg of whole RNA in Example 3-1 was mixed with 4 μl of 25 mM magnesium chloride, 2 μl of a solution of 10×PCR buffer consisting of 100 mM Tris-HCl buffer (pH 8.3) and 500 mM potassium chloride, 8 μl of 1 mM DNTP mix, 1 μl of a solution containing 1 unit/μl RNase inhibitor, 1 μl of a solution containing 2.5 units/μl reverse transcriptase, and 1 μl of 2.5 μM random hexamer, and further mixed with water to give a total volume of 20 μl. The mixed solution was placed in 0.5 ml reaction tubes, and, in the usual manner, successively incubated at 25° C. for 10 min, at 42° C. for 30 min, at 99° C. for 5 min, and at 5° C. for 5 min to effect the reverse transcriptase reaction, followed by recovering an aqueous solution containing the first strand cDNA.

To 20 μl of the aqueous solution, 4 μl of 25 mM magnesium chloride, 8 μl of 10×PCR buffer, 0.5 μl of a solution containing 2.5 units/μl of AmpliTaq DNA polymerase commercialized by Perkin-Elmer Corp., Instrument Div., Norwalk, Conn., USA, and 1 pmol each of primers 1 and 2 as a sense primer or an anti-sense primer were added. The mixture was made up to a volume of 100 μl with sterilized distilled water, and, in the usual manner, successively incubated at 94° C. for 1 min, at 45° C. for 2 min, at 72° C. for 3 min in a cyclic manner for 40 cycles to amplify a DNA fragment, which partially encodes the present polypeptide, by using the first strand cDNA as a template. Primers 1 and 2 were oligonucleotides which were chemically synthesized based on the amino acid sequences of Pro-Glu-Asn-Ile-Asp-Asp-Ile (corresponding to residues 10-16 of SEQ ID NO:1) and Phe-Glu-Asp-Met-Thr-Asp-Ile (corresponding to residues 4-10 of SEQ ID NO:2) and have the nucleotide sequences of 5'-ATRTCRTCDATRTTYTCNGG-3' (SEQ ID NO:9) and 5'-TTYGARGAYATGACNGAYAT-3' (SEQ ID NO:10).

A portion of the resultant PCR product was fractionated by electrophoresis on a 2 w/v % agarose gel, transferred onto a nylon membrane, fixed with 0.4 N sodium hydroxide, washed with 2×SSC, air dried, soaked in a prehybridization solution containing 5×SSPE, 5× Denhardt's solution, 0.5 w/v % SDS and 100 μg/ml of denatured salmon sperm DNA, and incubated at 65° C. for 3 hours. An oligonucleotide probe 1 having a nucleotide sequence of 5'TTYGARGA-RATGGAYCC-3' (SEQ ID NO:11) was synthesized based on the amino acid sequence of Phe-Glu-Glu-Met-Asp-Pro in (corresponding to residues 4-9 of SEQ ID NO:1), and labeled with [γ-$^{32}$P]ATP and T4 polynucleotide kinase. The nylon membrane was soaked in a solution containing 1 pmole of probe 1, 5×SSPE, 5 × Denhardt's solution, 0.5 w/v % SDS, and 100 μg/ml of a denatured salmon sperm DNA, and incubated at 45° C. for 24 hours to effect hybridization. The resultant nylon membrane was washed with 6×SSC and autoradiographed in the usual manner, revealing that the PCR product contained the desired DNA fragment.

The remaining PCR product was mixed with 50 ng of the pT7 BLUE T plasmid vector commercialized by Takara Shuzo Co., Ltd., Tokyo, Japan, an adequate amount of T4 ligase, and further mixed with 100 mM ATP to give a concentration of 1 mM, followed by incubation at 16° C. for 18 hours to insert the DNA fragment into the plasmid vector. The recombinant DNA thus obtained was introduced by the competent cell method into *Escherichia coli* NoVa Blue strain, a microorganism of the species *Escherichia coli* commercialized by Pharmacia LKB Biotechnology AB, Uppsala, Sweden, in order to obtain a transformant which was then inoculated onto an agar plate containing 10 g/l bactotryptone, 2.5 g/l sodium chloride, 15 g/l bacto-agar, 100 mg/l ampicillin, 40 mg/l X-Gal and 23.8 mg/l isopropyl-β-D-thiogalacto-pyranoside (abbreviated hereinafter as IPTG), and incubated at 37° C. for 24 hours to form colonies. A nylon membrane was overlaid on an agar medium plate in the usual manner and allowed to stand for about 30 seconds to attach the colonies to the nylon membrane. The nylon membrane was then detached from the plate and soaked for 7 min in a solution containing 0.5 N sodium hydroxide and 1.5 M sodium chloride to effect cell lysis. Thereafter, the nylon membrane was further soaked for 3 min in 0.5 M Tris-HCl buffer (pH 7.2) containing 1.5 M sodium chloride, washed with 2×SSC, soaked in 0.4 N sodium hydroxide for 20 min to fix the DNA, washed with 5×SSC, air-dried, soaked in a prehybridization solution containing 5×SSPE, 5 × Denhardt's solution, 0.5 w/v % SDS, and 100 μg/ml denatured salmon sperm DNA, and incubated at 65° C. for 3 hours. The colonies formed on the nylon membrane were hybridized with probe 1, washed with 6×SSC, and autoradiographed similarly as above, followed by selecting transformants which strongly hybridized to probe 1.

The transformants were inoculated into L-broth (pH 7.2) containing 100 μg/ml ampicillin and incubated at 37° C. for 18 hours, followed by collecting cells from the culture and isolating recombinant DNA by the conventional alkaline-SDS method. Analysis by the dideoxy method of nucleotide sequencing revealed that the recombinant DNA contained a DNA fragment consisting of the nucleotide sequence corresponding to nucleotides 85 to 281 of SEQ ID NO:3.

3-3: Preparation of mRNA 0.05 ml of an aqueous solution containing whole RNA in Example 3-1 was placed in a test tube, admixed with 0.5 ml of 10 mM Tris-HCl buffer (pH 7.5) containing 1 mM EDTA and 0.1 w/v % SDS, and made up to a volume of 1 ml with sterilized distilled water. To the mixture was added 1 ml OLIGOTEX-dT30 SUPER, an oligo-(dT)$_{30}$ latex commercialized by Nippon Roche K.K., Tokyo, Japan, followed by incubation at 65° C. for 5 min to denature the RNA and then cooling for 3 min in an ice-chilled bath. The resultant mixture was admixed with 0.2 ml of 5 M sodium chloride, incubated at 37° C. for 10 min, and centrifuged at 10,000 rpm at 25° C. for 10 min. The precipitate in the form of a pellet was suspended in 0.5 ml sterilized distilled water, and incubated at 65° C. for 5 min to extract mRNA from the oligo-(dT)$_{30}$ latex. The yield of the mRNA was about 5 μg.

3-4: Preparation of cDNA Library

A cDNA Library was prepared from the mRNA in Example 3-3 by using cDNA SYNTHESIZING SYSTEM PLUS, a cDNA cloning kit commercialized by Amersham Corp., Amersham International, Arlington Heights, Ill., USA. The procedures used are as follows: To a 1.5-ml reaction tube were successively added 4 μl of a solution for synthesizing the first strand cDNA, 1 μl sodium pyrophosphate solution, 1 μl of a solution of human placenta RNase inhibitor, 2 μl dNTP mix, and 1 μl oligo-$(dT)_{16}$ primer. The resultant mixture was mixed with 2 μg of mRNA from Example 3-3, made up to a volume of 19 μl with sterilized distilled water, mixed with 1 μl of a solution containing 20 units of reverse transcriptase, and incubated at 42° C. for 40 min to obtain a reaction mixture containing the first strand cDNA.

The reaction mixture obtained was mixed with 37.5 μl of a solution for synthesizing the second strand cDNA, 0.8 unit of ribonuclease H derived from *Escherichia coli*, 23 units of DNA polymerase I, and made up to a volume of 100 μl with sterilized distilled water. The resultant mixture was successively incubated at 12° C. for 60 min and at 22° C. for 60 min, mixed with 2 units of T4 DNA polymerase, and incubated at 37° C. for 10 min to obtain a reaction mixture containing the second strand cDNA. To the reaction mixture was added 4 μl of 0.25 M EDTA (pH 8.0) to terminate the reaction, and the resultant mixture was extracted with phenol/chloroform and treated with ethanol in the usual manner to precipitate the cDNA, followed by recovering the cDNA in the precipitate.

To the CDNA thus obtained were added in the following order: 2 μl of L/K buffer, 250 pmol EcoRI adaptor, and 2.5 units of T4 DNA ligase in this order. The resultant solution was made up to a volume of 20 μl with sterilized distilled water, and incubated at 15° C. for 16 hours to ligate the EcoRI adaptor to both ends of the CDNA. The reaction mixture was mixed with 2 μl of 0.25 M EDTA to inactivate the remaining enzyme, and subjected to molecular sieve chromatography to remove intact EcoRI adaptor. 40 μl of L/K buffer and 80 units of T4 polynucleotide kinase were added to the mixture, and the mixture was made up to a volume of 400 μl with sterilized distilled water, followed by incubation at 37° C. for 30 min to methylate the EcoRI cleavage sites. The resultant mixture was extracted with phenol/chloroform and treated with ethanol to precipitate the objective DNA, followed by recovery of the DNA. To the DNA were added 1.5 μl of L/K buffer containing an adequate amount of λgt10 arms, and 2.5 units of T4 DNA ligase. The resultant solution was made up to a volume of 15 μl with sterilized distilled water, incubated at 15° C. for 16 hours to effect ligation, and subjected to conventional in vitro packaging method to obtain a phage containing a recombinant λDNA.

3-5: Cloning of Recombinant DNA

A seed culture of *Escherichia coli* NM514 strain was infected with the phage from Example 3-4 in the usual manner, and the infected cells were inoculated onto an agar plate (pH 7.0) containing 10 g/l bacto-tryptone, 5 g/l bacto-yeast extract, 10 g/l sodium chloride and 15 g/l bacto-agar, and incubated at 37° C. for 16 hours to form plaques. The agar plate was covered with a nylon membrane and allowed to stand for about 30 seconds to attach the plaques to the nylon membrane. The nylon membrane was then detached from the plate, and successively soaked in an aqueous solution containing 0.5 M sodium hydroxide and 1.5 M sodium chloride for 7 min and in 0.5 M Tris-HCl buffer (pH 7.0) containing 1.5 M sodium chloride for 3 min. The nylon membrane was washed with 2×SSC, air dried, soaked in a solution containing 5×SSPE, 5× Denhardt's solution, 0.5 w/v % SDS, and 100 μg/ml denatured salmon sperm DNA, and incubated at 65° C. for 3 hours. Thereafter, the resultant nylon membrane was incubated in a solution containing an adequate amount of the DNA fragment obtained in Example 3-2 as probe 2 and labeled with $^{32}P$ by the READY PRIME DNA LABELLING SYSTEM, a DNA labeling kit commercialized by Amersham Corp., Amersham International, Arlington Heights, Ill., USA, in 5×SSPE, 5× Denhardt's solution, 0.5 w/v % SDS, and 100 μg/ml of denatured salmon sperm DNA, and incubated at 60° C. for 20 hours to effect hybridization. The resultant hybridized nylon membrane was subjected to autoradiography, similar to what was done above, to select phage DNA clones which strongly hybridized with probe 2.

Using conventional techniques, the clones were amplified in *Escherichia coli*, followed by extracting recombinant DNA from the cells. The recombinant DNA was then digested with the restriction enzyme EcoRI. Plasmid vector pUCl9 (ATCC 37254) was also digested with the same restriction enzyme, and the resultant digested DNA fragments and plasmid fragments were ligated together with DNA ligase to obtain a recombinant DNA which was then introduced into *Escherichia coli* JM109 strain (ATCC 53323) by the conventional competent cell method to obtain a transformed host cell.

3-6: Determination of Nucleotide and Amino Acid Sequences

The transformed *E. coli* host cell obtained in Example 3-5 was inoculated into L-broth (pH 7.2) and cultured at 37° C. for 13 hours with agitation. The resultant proliferated cells were collected and treated according to the conventional alkaline-SDS method to obtain a recombinant DNA containing the DNA according to the present invention. Analysis on an automatic sequencer using a fluorophotometer revealed that the recombinant DNA contains the nucleotide sequence from the 5'-terminus in SEQ ID NO:3. Further analysis of the nucleotide sequence indicated that it encodes the amino acid sequence containing the N-terminus in SEQ ID NO:4. The amino acid sequence contains the partial amino acid sequences of SEQ ID NOs:1 and 2 corresponding to residues 79 to 103 and from 26 to 43 in SEQ ID NO:4, and this means that the present polypeptide includes the amino acid sequence containing the N-terminus of SEQ ID NO:4, and that it is encoded by a DNA containing the nucleotide sequence from the 5'-terminus of SEQ ID NO:3.

In the following Examples 4 to 7, a cDNA, which encodes another polypeptide that induces the IFN-γ production by immunocompetent cells, is prepared from human liver mRNA by using a DNA fragment of the nucleotide sequence of SEQ ID NO:3 as probe. The nucleotide sequence of the cDNA was analyzed and was determined to encode the amino acid sequence of the polypeptide. The cDNA was expressed and produced in *Escherichia coli*, and the features and properties of the polypeptide produced were studied.

Example 4

Nucleotide and Amino Acid Sequence of Polypeptide 4-1: Preparation of cDNA Library A cDNA library was prepared from normal human liver tissue poly$(A)^+$to RNA, a product commercialized by ClonatecBIOSOFT, Paris Cedex, France, by using a cDNA cloning kit, cDNA SYNTHESIZING SYSTEM PLUS, commercialized by Amersham Corp., Amersham International, Arlington Heights, Ill., USA. The procedures used are as follows: To a 1.5 ml reaction tube were successively added 10 µl of a solution for synthesizing the first strand cDNA, 2.5 µl of 1 mM sodium pyrophosphate, 2.5 µl of a solution containing 1 µg/µl of a human placenta ribonuclease inhibitor, 5 µl of a solution containing 1 µg/µl of a dNTP mix, 2.5 µl of a solution containing 1 µg/µl oligo-dT primer, 5 µg of normal human liver tissue poly(A)$^+$ RNA, and made up to a volume of 45 µl with sterilized distilled water. Thereafter, the resultant mixture was mixed with 5 µl of a solution containing reverse transcriptase, and incubated at 42° C. for 40 min to obtain a reaction mixture containing the first strand cDNA.

To the reaction mixture was added 93.5 µl of a solution for synthesizing the second strand cDNA, 4 units of RNaseH derived from *Escherichia coli*, 115 units of DNA polymerase, and made up to a volume of 250 µl with sterilized distilled water. The resultant mixture was successively incubated at 12° C. for 60 min, at 22° C. for 60 min, and at 70° C. for 10 min, mixed with 10 units of T4 polymerase, and further incubated at 37° C. for 10 min. To the reaction mixture was added 10 µl of 0.25 M EDTA (pH 8.0) to terminate the reaction, and the resultant mixture was extracted with phenol/chloroform, and treated with ethanol to precipitate the objective double stranded cDNA in the usual manner, followed by recovering the precipitate.

To the double stranded cDNA thus obtained were added 2 µl L/K buffer (pH 8.0), 250 pmol EcoRI adaptor, and 2.5 units of T4 DNA ligase, and the resultant solution was made up to a volume of 20 µl with sterilized distilled water, and incubated at 15° C. for 16 hours to ligate the EcoRI adaptor to both ends of the cDNA. The resultant mixture was then mixed with 2 µl of 0.25 M EDTA to terminate the reaction, and subjected to molecular sieve chromatography to remove unligated EcoRI adaptor. 40 µl of L/K buffer (pH 8.0) and 80 units of T4 polynucleotide kinase were added to the resultant mixture and the mixture was made up to a volume of 400 µl with sterilized distilled water, followed by incubation at 37° C. for 30 min to methylate the EcoRI cleavage sites. The resultant mixture was extracted with phenol/chloroform and treated with ethanol to precipitate the objective cDNA, followed by recovering the cDNA. To the cDNA were added 1.5 µl of L/K buffer (pH 8.0) containing an adequate amount of λgt10 arms, and 2.5 units of T4 DNA ligase, and the resultant solution was made up to a volume of 15 µl with sterilized distilled water, incubated at 15° C. for 16 hours to effect ligation, and subjected to conventional in vitro packaging method to obtain a phage containing recombinant λDNA.

4-2: Cloning of Recombinant DNA

A seed culture of *Escherichia coli* NM514 strain was infected with the phage in Example 4-1, and the infected cells were inoculated onto an agar plate (pH 7.0) containing 10 g/l bacto-tryptone, 5 g/l bacto-yeast extract, 10 g/l sodium chloride, and 15 g/l bacto-agar, and incubated at 37° C. for 16 hours to form plaques. According to conventional methods, the agar plate was covered with a nylon membrane and allowed to stand for about 30 seconds to attach the plaques thereto. Thereafter, the nylon membrane was detached from the plate, and successively soaked in an aqueous solution containing 0.5 N sodium hydroxide and 1.5 M sodium chloride for 7 min and in 0.5 M Tris-HCl buffer (pH 7.0) containing 1.5 M sodium chloride for 3 min. The nylon membrane was washed with 5×SSC, air-dried, soaked in a solution containing 5×SSPE, 5× Denhardt's solution, 0.5 w/v % SDS and denatured salmon sperm DNA, and incubated at 65° C. for 3 hours. To clone the objective recombinant DNA, a DNA fragment having the nucleotide sequence of SEQ ID NO:3 was labeled with $^{32}$P using the READY PRIME DNA LABELLING SYSTEM, a DNA labeling kit commercialized by Amersham Corp., Amersham International, Arlington Heights, USA, and designated as probe 3. The procedures used are as follows: Place 25 ng of a DNA fragment prepared by the method in Example 3-5 in a 1.5 ml reaction tube, made up to a volume of 45 µl with sterilized distilled water, incubated at 95° C. for 3 min, and transferred to another reaction tube. Five µl of an [α-$^{32}$P] dCTP solution was added to the reaction tube, and the DNA fragment was labeled according to the instruction attached to the kit by incubating it at 37° C. for 30 min. Thereafter, the resultant product containing the labeled DNA fragment was subjected to conventional molecular sieve chromatography to remove unincorporated [α-$^{32}$P] dCTP.

The above nylon membrane was soaked in a solution containing 5×SSPE, 5× Denhardt's solution, 0.5 w/v % SDS, and 100 µg/ml of a denatured salmon sperm DNA, and the mixture was incubated at 60° C. for 20 hours to effect hybridization, and further washed at ambient temperature in 6×SSC for 20 min and in 2×SSC for 20 min. The resultant hybridized nylon membrane was subjected to autoradiography to select phage DNA clones which strongly hybridized with probe 3.

With conventional techniques, the DNA clones were amplified in *Escherichia coli*, and the recombinant DNA was extracted from the cells. The recombinant DNA was digested with the restriction enzyme EcoRI. Plasmid vector pUC19 (ATCC 37254) was digested with the same restriction enzyme, and the cleaved DNA fragments and plasmid fragments were ligated with DNA ligase to obtain a recombinant DNA which was then introduced into *Escherichia coli* JM109 strain (ATCC 53323) by the conventional competent cell method to obtain a transformant containing the present DNA.

4-3: Determination of Nucleotide Sequence and Amino Acid Sequence

The transformant obtained in Example 4-2 was inoculated into L-broth (pH 7.2) containing 50 µg/ml of ampicillin, and cultured at 37° C. for 18 hours with agitation. The proliferated cells were collected by centrifugation and treated according to the conventional alkaline-SDS method to extract the recombinant DNA. The analysis of the nucleotide sequence on an automatic sequencer using a fluorophotometer revealed that the recombinant DNA contains the nucleotide sequence of SEQ ID NO:7. The amino acid sequence deduced from the nucleotide sequence is shown as SEQ ID NO:8, indicating that the present polypeptide includes the amino acid sequence of SEQ ID NO:6, and that the polypeptide is encoded by the DNA of nucleotide sequence SEQ ID NO:5. In SEQ ID NO:8, Xaa represents isoleucine or threonine.

Example 5

Preparation of Replicable Recombinant DNA and Transformants

To a 0.5 ml reaction tube were added 8 µl of 25 mM magnesium chloride, 10 µl of 10×PCR buffer, 8 µl of 1 mM dNTP mix, 0.5 µl of a solution containing 2.5 units/µl AmpliTaq DNA polymerase, and 1 ng of the recombinant DNA of Example 4-2. The resultant mixture was mixed with adequate amounts of two oligonucleotides, as a sense primer or an anti-sense primer, having the nucleotide sequences represented by 5'-CGAGGGATCCTACTTTG-GCAAGCTTG-3' (SEQ ID NO:12) and 5'-CAAGGAAT-TCCTAGTCTTCGTTTTG-3' (SEQ ID NO:13), which had been chemically synthesized based on the nucleotide sequences encoding the amino acid residues near the N- and C-termini in SEQ ID NO:5, and made up to a volume of 100 µl with sterilized distilled water. The resultant mixture was successively incubated at 94° C. for 1 min, at 60° C. for 2 min, and at 72° C. for 3 min, and this incubation cycle was repeated for 40 times to obtain a PCR product which was then digested with restriction enzymes BamHI and EcoRI to obtain a BamHI-EcoRI DNA fragment. The resultant BamHI-EcoRI DNA fragment was mixed with an adequate amount of sterilized distilled water. The solution was then mixed with 10 ng of a plasmid vector, pGEX-2T (commercialized by Pharmacia LKB Biotechnology AB, Uppsala, Sweden), which had been previously digested with BamHI and EcoRI as restriction enzymes, 10 µl of 10× ligation buffer, and an adequate amount of T4 DNA ligase and 10 mM ATP to give a final concentration of 1 mM, followed by incubation at 16° C. for 18 hours to obtain the replicable recombinant DNA, pHIGIF.

Figure 2:
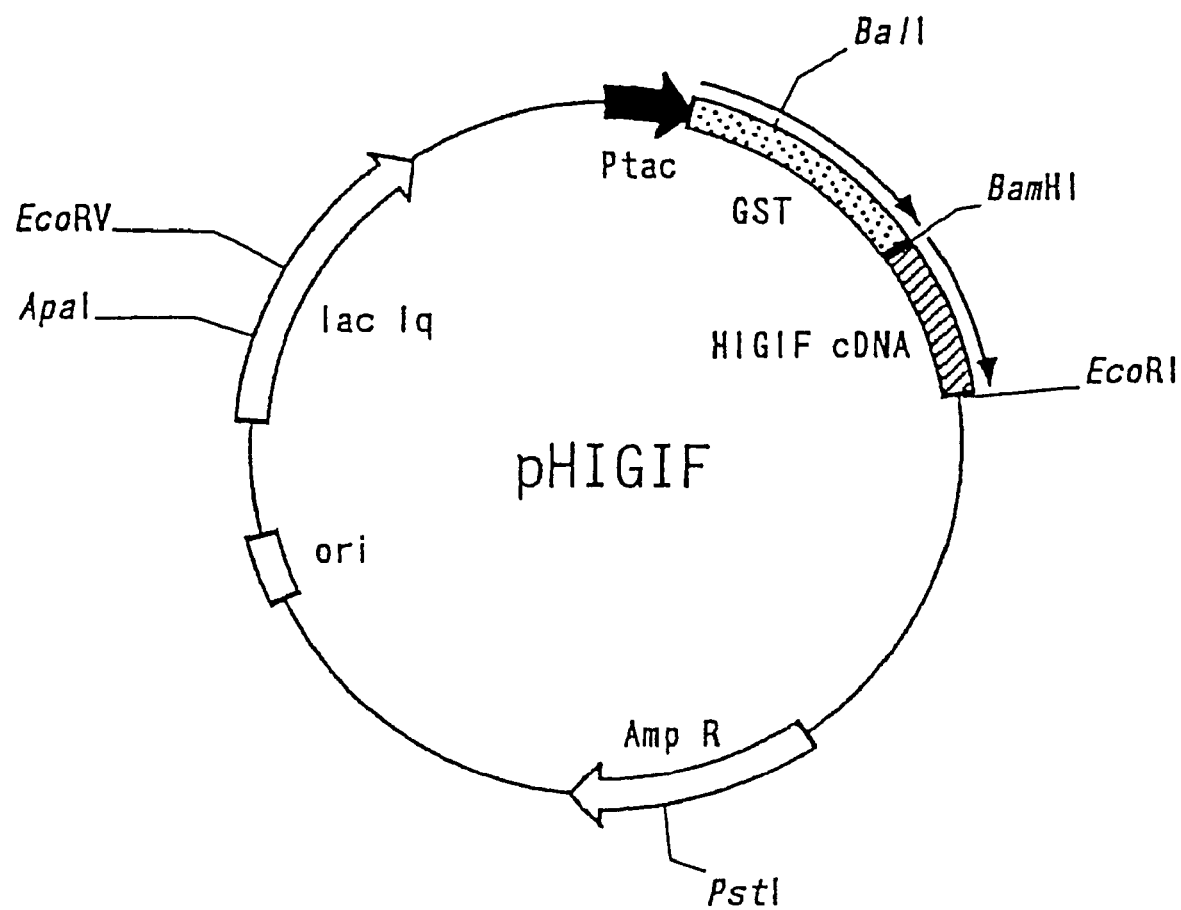
FIG. 2 is a schematic representation of the structure of recombinant plasmid pHIGIF, where HIGIF cDNA represents the cDNA encoding the INF-γ inducing polypeptide, Ptac represents the tac promoter, GST represents glutathione S transferase gene, AmpR represents ampicillin resistance gene, and ori represents an *Escherichia coli* replication initiation site present on plasmid pBR322.

The recombinant DNA PHIGIF was introduced by conventional competent cell method into *Escherichia coli* DH5α strain commercialized by Toyobo Co., Ltd., Tokyo, Japan, and the resultant transformant HIGIF was inoculated into L-broth (pH 7.2) containing 50 µg/ml ampicillin, and incubated at 37° C. for 18 hours with agitation. The resultant culture was centrifuged to obtain the proliferated transformants, which were then subjected to conventional alkaline-SDS method to extract the recombinant DNA pHIGIF. The analysis of the recombinant PHIGIF by the dideoxy method revealed that as shown in FIG. 2, HIGIF cDNA or the cDNA in SEQ ID NO:5 are ligated into the sites downstream of the sequences for the Tac promotor and glutathione S-transferase gene.

Example 6

Production of Polypeptide from the Transformant

The transformant HIGIF from Example 5 was inoculated into T-broth (pH 7.2) containing 50 µg/ml of ampicillin, and incubated at 37° C. for 18 hours with agitation to obtain a seed culture. Eighteen L aliquots of a fresh preparation of T-broth (pH 7.2) were placed in 30-L jar fermenters, inoculated with 1 v/v % of the seed culture, and cultured at 37° C. under aeration agitation conditions. During cultivation, the culture was sampled and monitored for absorbance at a wavelength of 650 nm, and when the absorbance reached approximately 1.5, IPTG was added to the culture to give a concentration of 0.1 mM. Thereafter, the culture was further incubated for another 5 hours and centrifuged to separate cells from the culture. The cells were suspended in a solution (pH 7.2) containing 139 mM sodium chloride, 7 mM disodium hydrogen phosphate, and 3 mM sodium dihydrogen phosphate, treated with ultrasound in the usual manner and centrifuged to obtain a supernatant.

The supernatant was fed to a column packed with GLU-TATHIONE SEPHAROSE 4B, a product of Pharmacia LKB Biotechnology AB, Uppsala, Sweden, which had been previously equilibrated with a solution (pH 7.2) containing 139 mM sodium chloride, 7 mM disodium hydrogen phosphate and 3 mM sodium dihydrogen phosphate. The column was washed with a fresh preparation of the same solution, and 100 U of thrombin was added to 1 ml of the gel in the column to effect an enzymatic cleavage reaction while allowing the column to stand at ambient temperature for 16 hours. The column was fed with a fresh preparation of the same solution above to elute the reaction product, and the eluate was fed to a column packed with SUPERDEX 75, a product of Pharmacia LKB Biotechnology AB, Uppsala, Sweden, followed by collecting fractions corresponding in size to about 18,500 daltons. The fractions were pooled, concentrated and lyophilized to obtain a solid product containing the present polypeptide in a yield of about 80 µg per L of culture.

Example 7

Physicochemical Property of Polypeptide 7-1: Molecular Weight

In accordance with the method reported by U. K. Laemmli in *Nature*, 227:680-685 (1970), the purified polypeptide prepared in Example 6 was electrophoresed on a sodium dodecyl sulfate (SDS) polyacrylamide gel free of reducing agent to show mainly a single protein band with IFN-γ inducibility at a position corresponding to about 18,500±3,000 daltons. The marker proteins used in this experiment were calf serum albumin (MW=67,000 daltons), ovalbumin (MW=45,000 daltons), soy bean trypsin inhibitor (MW=20,100 daltons), and α-lactalbumin (MW=14,400 daltons).

7-2: Isoelectric Point

The purified polypeptide in Example 6 was chromatofocused and exhibited an isoelectric point of about 4.9±1.0.

7-3: Amino Acid Sequence Containing the N-terminus

The purified polypeptide from Example 6 was analyzed on a MODEL 473 A protein sequencer commercialized by Perkin-Elmer Corp., Instrument Div., Norwalk, Conn., and revealed that it had the structure where a peptide, "Gly-Ser-", is coupled to the tyrosine residue at the N-terminus of the amino acid sequence of SEQ ID NO:14 by the fusion with glutathione S-transferase and by the cleavage with thrombin.

7-4(a): Biological Activity

Spleen cells from 8 week old female C3H/HeJ mice were excised and suspended in serum-free RPMI 1640 medium (pH 7.4), and the resultant cells were washed with a fresh preparation of the same medium, and soaked in Gey solution (pH 8.0) to effect hemolysis. The resultant spleen cells were suspended in RPMI 1640 medium (pH 7.4) supplemented with 10 v/v % fetal serum to give a cell density of $1 \times 10^7$ cells/ml. Ten ml aliquots of the cell suspension were distributed into plastic petri dishes, 9 cm in diameter, and incubated at 37° C. for 1 hour in a 5 v/v % $CO_2$ incubator. Only cells floating in the resultant cultures were collected and washed with RPMI 1640 medium (pH 7.4) supplemented with 10 v/v % fetal bovine serum for use in the following test for IFN-γ induction.

Mouse spleen cells were suspended in RPMI 1640 medium (pH 7.4) supplemented with 10 v/v % fetal calf serum to give a cell density of $1 \times 10^7$ cells/ml, and 0.15 ml aliquots of which were distributed to 96-well microplates. 0.05 ml of a solution of a purified polypeptide from Example 6 diluted with a fresh preparation of the same medium was added to each well, and the cells were incubated with or without the addition of 0.05 ml of 2.5 µg/ml concanavalin A or 50 units/ml interleukin 2, at 37° C. for 24 hours in a 5 v/v % CO$_2$ incubator. After completion of the culture, 0.1 ml of the resultant supernatant in each well was sampled to assay the activity of the formed IFN-γ by enzyme immunoassay. As a control, a system similar to the system above was provided and similarly treated as above except that the purified polypeptide, concanavalin A and interleukin 2 were not used. As an IFN-γ standard, a mouse IFN-γ preparation Gg02-901-533, obtained from the National Institutes of Health, Bethesda, Md., USA was used and the activity of IFN-γ was expressed in international units (IU). The results are shown in Table 1.

TABLE 1

| Sample concentration (μg/ml) | IFN-γ production by mouse spleen cell (IU/ml) | | |
|---|---|---|---|
| | Sample | Sample plus concanavalin A | Sample plus interleukin 2 |
| 10.00 | 12 | 138 | 118 |
| 3.33 | 6 | 88 | 55 |
| 1.11 | 5 | 56 | 16 |
| 0.37 | 5 | 21 | 12 |
| 0.12 | 5 | 12 | 10 |
| 0.04 | 5 | 11 | 7 |
| 0 | 0 | 4 | 1 |

Note:
In the Table, Sample means the present polypeptide.

7-4(b): Induction of IFN-γ Production from Human Lymphocyte

By using a syringe containing heparin, blood was collected from a healthy donor, which was then diluted two-fold with serum-free RPMI 1640 medium (pH 7.4), and overlaid onto FICOLL in a centrifuge tube. Lymphocytes obtained by centrifugation at 2,000 rpm for 20 min were then washed with RPMI 1640 medium (pH 7.4) supplemented with 10 v/v % fetal calf serum, suspended in a fresh preparation of the same medium to give a cell density of 5×10$^6$ cells/ml, and treated similarly as in Example 7-4(a) except that a human IFN-γ standard, Gg23-901-530, obtained from the National Institutes of Health, Bethesda, Md., USA, was used as an IFN-γ standard. The results are shown in Table 2.

TABLE 2

| Sample concentration (μg/ml) | IFN-γ production by human lymphocyte (IU/ml) | | |
|---|---|---|---|
| | Sample | Sample plus concanavalin A | Sample plus interleukin 2 |
| 10.00 | 191 | 479 | 1,182 |
| 3.33 | 169 | 576 | 1,419 |
| 1.11 | 168 | 426 | 1,106 |
| 0.37 | 150 | 296 | 739 |
| 0.12 | 74 | 193 | 390 |
| 0.04 | 36 | 137 | 324 |
| 0 | 1 | 11 | 24 |

Note:
In the Table, Sample means the present polypeptide.

The results in Tables 1 and 2 demonstrate that the present polypeptide has an activity of inducing IFN-γ production by immunocompetent cells of mammals including human and mouse. In the control groups, no significant IFN-γ production was found, while in the systems in which the present polypeptide was present, significant IFN-γ production was observed. This activity of the polypeptide was strongly augmented when used in combination with concanavalin A or interleukin 2 as a cofactor.

Example 8

Preparation of Polypeptide

The immunoreaction of newborn hamsters were suppressed in a conventional manner by injecting a rabbit antiserum against hamster thymus into the hamsters, transplanting to their dorsal subcutaneous tissues with about 5×10$^5$ cells/hamster of THP-1 cells (ATCC TIB202), a myelomonocytic cell line of a human acute monocytic leukemia, and fed for three weeks in a conventional manner. Tumor masses that formed in subcutaneous tissues, about 15 g by weight per hamster, were extracted, dispersed in a conventional manner in physiological saline, and washed with phosphate buffered saline (PBS).

The propagated cells thus obtained were washed with ten volumes of cold 20 mM HEPES buffer (pH 7.4) containing 10 mM potassium chloride, 1.5 mM magnesium chloride, and 0.1 mM EDTA, allowed to stand in three volumes of a fresh preparation of the same buffer under ice chilled conditions, frozen at −80° C., and thawed to disrupt the cells. The disrupted cells were centrifuged to obtain a supernatant which was then fed to a column packed with DEAE-SEPHAROSE (a gel for ion-exchange column chromatography commercialized by Pharmacia LKB Biotechnology AB, Uppsala, Sweden) previously equilibrated with 10 mM phosphate buffer (pH 6.6), followed by washing the column with 10 mM phosphate buffer (pH 6.6), eluting with a sodium chloride which is increased stepwise from 0 M to 0.5 M in 10 mM phosphate buffer (pH 6.6), and collecting a fraction which elutes at about 0.2 M sodium chloride.

The collected fraction was dialyzed against 10 mM phosphate buffer (pH 6.8) and fed to a column packed with DEAE 5PW previously equilibrated with the buffer (a gel for ion-exchange chromatography commercialized by Tosoh Corporation, Tokyo, Japan), followed by eluting with a sodium chloride gradient which was increased from 0 M to 0.5 M in 10 mM phosphate buffer (pH 6.8), and collecting fractions which eluted at about 0.2-0.3 M sodium chloride.

The collected fractions were pooled, dialyzed against PBS, fed to a plastic cylindrical immunoaffinity chromatography column packed with a gel containing a monoclonal antibody which had been prepared according to the method disclosed in Japanese Patent Application No.58,240/95 (applied for by the present applicant and which corresponds to U.S. Ser. No. 08/555,818), and washed with PBS. The column was fed with 100 mM glycine-HCl buffer (pH 2.5) to collect eluate fractions which contained a polypeptide that induces IFN-γ production by immunocompetent cells. The fractions collected were pooled, dialyzed against sterile distilled water, concentrated with a membrane filter, and lyophilized to obtain a purified solid polypeptide with a yield of about 50 ng per hamster.

Example 9

Molecular Weight

In accordance with the method reported by U. K. Laemmli, Nature, 227:680-685 (1970), a purified polypeptide prepared by the method disclosed in Example 8 was electrophoresed on SDS-PAGE in the presence of 2 w/v % dithiothreitol, and a main protein band with an IFN-γ inducibility was observed at a position corresponding to a molecular weight of about 18,000-19,500 daltons. The proteins used as markers were bovine serum albumin (MW=67,000 daltons), ovalbumin (MW=45,000 daltons), carbonic anhydrase (MW=30,000 daltons), soy bean trypsin inhibitor (MW=20,100 daltons), and α-lactalbumin (MW=14,400 daltons).

Example 10

Amino Acid Sequence and Peptide Mapping in the N-terminal Region 10-1: Amino Acid Sequence Near at the N-terminus
The purified polypeptide of Example 8 was analyzed on a MODEL 473A protein sequencer commercialized by Perkin-Elmer Corp., Norwalk, Conn., and it was found to have the amino acid sequence of SEQ ID NO:14, and in particular, SEQ ID NO:18.

10-2: Peptide Mapping
A purified polypeptide obtained by the method in Example 8 was dissolved in an adequate amount of sterile distilled water, and the solution was fed to a column packed with ASAHIPAK® C4P-50 4E (a gel for high-performance liquid chromatography (HPLC) commercialized by Showa Denko, K.K., Tokyo, Japan) which had been previously equilibrated with 0.1 v/v % aqueous trifluoroacetic acid solution. The column was washed with 0.1 v/v % aqueous trifluoroacetic acid solution and a linear gradient solution of acetonitrile from 0 v/v % to 90 v/v % in a solution of a mixture of trifluoroacetic acid and acetonitrile was fed to the column at a flow rate of 60 ml/hour. Eluted fractions containing a polypeptide which induces the IFN-γ production by immunocompetent cells were collected, pooled, neutralized with 1 M aqueous Tris solution (pH 11.2), and concentrated in a conventional manner. To 50 mM Tris-HCl buffer (pH 8.5), in which was dissolved an adequate amount of clostripain (commercialized by Sigma Chemical Company, St. Louis, Mo., USA), the polypeptide was added in an amount of about 50 times that of clostripain on the basis of molar ratio while removing acetonitrile, and the resulting mixture was allowed to react at a pH of 8-9 and at 37° C. for 12 hours to obtain a reaction mixture containing fragments of the polypeptide.

Figure 3:
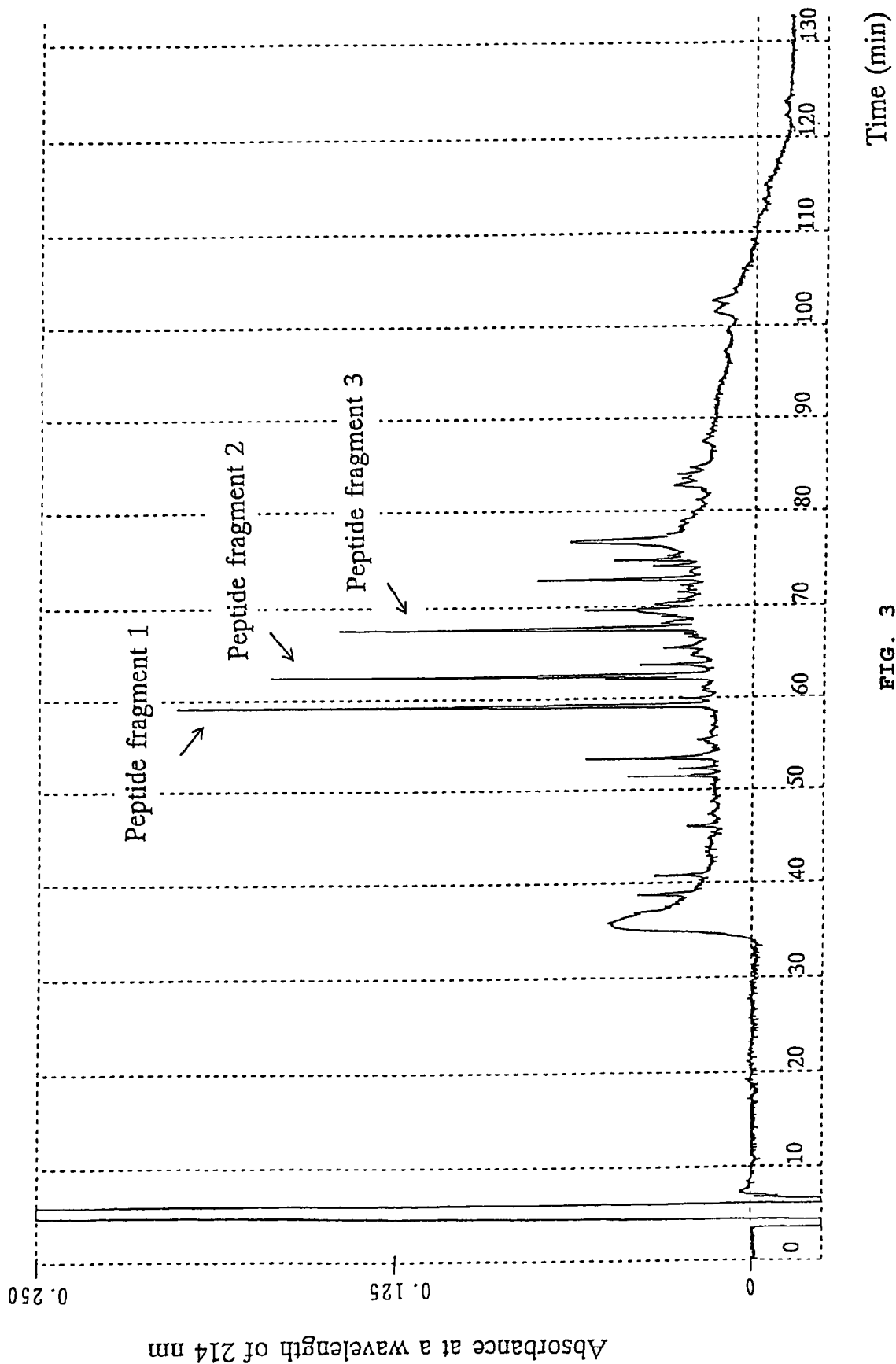
FIG. 3 is an HPLC elution pattern/profile of peptide fragments obtained by peptide mapping an INF-γ inducing protein of human cell origin using clostripain.

The reaction mixture was fed to a column packed with ODS-120T (a gel for HPLC commercialized by Tosoh Corporation, Tokyo, Japan), which had been previously equilibrated with 0.1 v/v % aqueous trifluoroacetic acid solution. The column was washed with 0.1 v/v % aqueous trifluoroacetic acid solution and a linear gradient solution of acetonitrile from 0 v/v % to 70 v/v % in a solution of a mixture of trifluoroacetic acid, acetonitrile and water (where the concentration of trifluoroacetic acid was 0.09 v/v %) was fed at a flow rate of 30 ml/hour while monitoring the absorption level of the peptide, i.e., the concentration of the peptide, at a wave length of 214 nm. FIG. 3 shows the resulting peptide map.

In FIG. 3, peptide fragments eluted at about 59, 62 and 68 min after initiating the elution are designated peptide fragments 1, 2 and 3, respectively. These peptide fragments were separately collected and analyzed for amino acid sequence on MODEL 473A, a protein sequencer commercialized by Perkin-Elmer Corp., Norwalk, Conn., in a conventional manner. As a result, it was found that peptide fragments 1 and 2 have the amino acid sequences of SEQ ID NOs:15 and 19, respectively, and peptide fragment 3 has the amino acid sequences of SEQ ID NOs:16 and 17. Comparison of these amino acid sequences with SEQ ID NO:6 revealed that peptide fragments 1 to 3 correspond to the residue positions 148-157, 1-13, and 45-58 and 80-96, respectively, in the amino acid sequence of SEQ ID NO:6. These results confirmed that polypeptide fragments 1 and 2 correspond to the C- and N-terminal fragments of the polypeptide used for analysis, and that polypeptide fragment 3 corresponds to an internal fragment of the polypeptide.

It is concluded that the purified polypeptide obtained by the method in Example 8 contains the amino acid sequence of SEQ ID NO:6 because Example 9 found that the purified polypeptide has a main protein band at a position corresponding to a molecular weight of about 18,000-19,500 daltons on SDS-PAGE, and the purified polypeptide is calculated to have a molecular weight of 18,199 daltons from the amino acid sequence of SEQ ID NO:6.

Example 11

Biological Activity 11-1: IFN-γ Production by Immunocompetent Cell
A blood sample taken from a healthy volunteer with a heparinized syringe was diluted two-fold with serum-free RPMI 1640 medium (pH 7.4). The diluted blood was overlaid onto FICOLL (commercialized by Pharmacia LKB Biotechnology AB, Uppsala, Sweden), followed by centrifugation to collect lymphocytes. These lymphocytes were washed with RPMI 1640 medium (pH 7.4) supplemented with 10 v/v % fetal bovine serum and suspended in a fresh preparation of the same medium to give a cell density of $1\times10^6$ cells/ml. The cell suspension was distributed to a 96-well microplate at a volume of 0.15 ml/well.

A purified polypeptide obtained by the method in Example 8 was diluted with RPMI 1640 (pH 7.4) supplemented with 10 v/v % fetal bovine serum, and the dilution was distributed to the above microplate at a volume of 0.05 ml/well. A fresh preparation of the same medium, either with or without 2.5 μg/ml Con A or 50 units/ml of a recombinant human interleukin 2 in a volume of 0.05 ml/well, was added to the microplate, and the microplate was incubated at 37° C. for 24 hours in a 5 v/v % $CO_2$ incubator. After completion of the culture, 0.1 ml of a culture supernatant was sampled from each well and assayed for IFN-γ activity by conventional enzyme immunosorbent assay (EIA). As a control, a system free of the purified protein was provided and treated similarly as above. The results are shown in Table 3 where the IFN-γ content was assayed and expressed in terms of international unit (IU) with respect to Gg23-901-530, an international standard for IFN-γ obtained from the National Institutes of Health, Bethesda, Md., USA.

TABLE 3

| Polypeptide concentration (ng/ml) | IFN-γ yield (IU/ml) | | |
|---|---|---|---|
| | Polypeptide | Polypeptide plus Con A | Polypeptide plus interleukin 2 |
| 0 | <0.5 | <2 | <0.5 |
| 0.32 | <0.5 | 6 ± 2 | 2 ± 1 |
| 1.6 | 10 ± 2 | 70 ± 20 | 60 ± 20 |
| 8 | 140 ± 10 | 490 ± 80 | 570 ± 30 |
| 40 | 180 ± 20 | 620 ± 10 | 880 ± 50 |
| 200 | 260 ± 20 | 800 ± 20 | 1500 ± 400 |

Note:
In the table, the term Polypeptide means the present polypeptide.

The results in Table 3 show that, lymphocytes as immunocompetent cells, produced IFN-γ by the action of the present polypeptide. It is evident from the results that IFN-γ production is increased by the presence of interleukin 2 or Con A as a cofactor.

11-2: Increase of Cytotoxicity by NK Cell

A blood sample taken from a healthy volunteer with a heparinized syringe was diluted two-fold with PBS. The diluted blood was overlaid onto FICOLL and centrifuged to obtain a high density layer of lymphocytes. The lymphocytes were suspended in RPMI 1640 medium (pH 7.2) containing 10 μg/ml kanamycin, $5 \times 10^{-5}$ M 2-mercaptoethanol and 10 v/v % fetal bovine serum, and the suspension was distributed to a 12-well microplate at a volume of 0.5 ml/well. A purified polypeptide obtained by the method in Example 8 was appropriately diluted with a fresh preparation of the same medium, and the dilution was distributed to the same microplate at a volume of 1.5 ml/well, followed by adding 0.5 ml/well of a fresh preparation of the same buffer, either with or without 50 units/ml of a recombinant human interleukin 2, to the microplate, incubating the microplate at 37° C. for 24 hours in a 5 v/v % $CO_2$ incubator, and washing the resultant cells with PBS to obtain cultured lymphocytes containing NK cells as an effector cell. $1 \times 10^4$ cells/well aliquots of K-562 cells (ATCC CCL243), derived from human chronic myelocytic leukemia as an NK-cell susceptive target cell, and which had been labelled with $^{51}Cr$ in a conventional manner, were distributed to a 96-well microplate, and mixed with the above NK cells in a ratio of 2.5:1, 5:1 or 10:1 (effector cells:target cells). The microplate was incubated at 37° C. for 4 hours in a 5 v/v % $CO_2$ incubator, followed by counting the level of radioactivity present in each supernatant to count dead target cells. In each system, the percentage (%) of dead target cells with respect to total target cells used in this example was calculated to evaluate cytotoxicity. The results are shown in Table 4.

TABLE 4

| Polypeptide concentration | Concentration of interleukin 2 | Cytotoxicity Effector cells/ Target cells | | |
|---|---|---|---|---|
| (pM) | (Units/ml) | 2.5/1 | 5/1 | 10/1 |
| 0 | 0 | 19 | 36 | 59 |
| 0 | 10 | 28 | 44 | 61 |
| 0.5 | 0 | 22 | 41 | 63 |
| 0.5 | 10 | 31 | 54 | 69 |
| 5 | 0 | 28 | 49 | 66 |
| 5 | 10 | 36 | 58 | 71 |
| 50 | 0 | 29 | 53 | 67 |
| 50 | 10 | 42 | 62 | 72 |
| 500 | 0 | 33 | 56 | 84 |
| 500 | 10 | 57 | 76 | 96 |

Note:
In the table, the symbol (pM) means $10^{-12}$ M and the term Polypeptide means the present polypeptide.

The results in Table 4 show that the polypeptide according to the present invention has a property of enhancing the cytotoxicity by NK cells. As evident from the results, the cytotoxicity is further enhanced by the presence of interleukin 2.

11-3: Induction of LAK Cell Formation $1 \times 10^4$ cells/well aliquots of Raji cell (ATCC CCL86), a human Burkitt's lymphoma as an NK-cell non-susceptive target cell and which had been labelled with $^{51}Cr$ in a conventional manner were distributed to a 96-well microplate, and mixed with a cell suspension of the target cells and cultured lymphocytes containing LAK cells as an effector cell, similarly prepared as in the method in Example 11-2 (except for culturing 72 hours), in a ratio of 5:1, 10:1 or 20:1 (effector cells:target cells), followed by incubating the microplate at 37° C. for 4 hours in a 5 v/v % $CO_2$ incubator and counting the level of radioactivity present in each supernatant in a conventional manner. Thereafter, the cytotoxicity (%) was calculated in a manner similar to that in Example 11-2. The results are shown in Table 5.

TABLE 5

| Protein concentration | Concentration of interleukin 2 | Cytotoxicity Effector cells/ Target cells | | |
|---|---|---|---|---|
| (pM) | (Units/ml) | 5/1 | 10/1 | 20/1 |
| 0 | 0 | 12 | 23 | 31 |
| 0 | 10 | 14 | 25 | 35 |
| 0.5 | 0 | 14 | 24 | 34 |
| 0.5 | 10 | 18 | 32 | 42 |
| 5 | 0 | 16 | 26 | 37 |
| 5 | 10 | 21 | 36 | 50 |
| 50 | 0 | 22 | 41 | 49 |
| 50 | 10 | 26 | 52 | 56 |
| 500 | 0 | 27 | 44 | 61 |
| 500 | 10 | 33 | 59 | 72 |

Note:
In the table, (pM) represents means $10^{-12}$ M and the term Polypeptide means the present polypeptide.

The results in Table 5 show that the present polypeptide has a property of inducing LAK-cell formation. As evident from these results, this induction is further enhanced by the presence of interleukin 2.

Example 12

Acute Toxicity Test

A purified polypeptide obtained by the method in Example 8 was injected percutaneously, orally or intraperitioneally into 8 week-old mice in a conventional manner. The $LD_{50}$ of the polypeptide was found to be about 1 mg/kg mouse or higher and independent of the route of administration. This demonstrates that the present polypeptide is safe to incorporate into medicaments for administration to humans.

It is well known that IFN-γ is involved in the inhibition of bacterial infection, in the propagation of malignant tumors, in the regulation of human biophylaxis through the immunoregulatory function, and in the inhibition of immunoglobulin E antibody production. As discussed above, IFN-γ is now commercially available and is used as an agent for human diseases susceptible to treatment with IFN-γ, and the diseases to be treated, the dose, the administration, and the safety are almost revealed. It is reported in *Cytokines in Cancer Therapy*, edited by Frances R. Balkwill, translated by Yoshihiko WATANABE, published by Tokyo-Kagaku-Dojin, Tokyo, Japan (1991), that treatments using killer cells such as NK- and LAK-cells are used as anti-tumor immunotherapy and applied to human diseases, where most killer cells were reported to exert a satisfactory therapeutic effect. Recently, attention has focused on the relationship between the therapeutic effect and the augmentation of cytotoxicity of killer cells or the induction of the formation of killer cells using cytokines. For example, T. Fujioka et al. reported in *British Journal of Urology*, 73:23-31 (1994) that interleukin 2 strongly induced the formation of LAK cells in an anti-tumor immunotherapy using LAK cells and interleukin 2, and exerted a satisfactory effect on the metastasis of human cancer without substantially inducing serious toxicity and side effects.

Thus, IFN-γ and killer cells are closely related with regard to the treatment and the prevention of human diseases for complete cure and remission. With this relationship shown by the results in Examples 11 and 12, the fact that the present polypeptide induces the IFN-γ production by immunocompetent cells, enhances the cytotoxicity of NK cells, and induces the LAK cell formation indicates that a pharmaceutical composition containing the present polypeptide can be administered to humans over a relatively long period of time and can exert a satisfactory therapeutic effect on the treatment and the prevention of IFN-γ-related and/or killer cell-related diseases without substantially inducing serious side effects. Examples 13-1 to 13-8 below describe preferred embodiments for the preparation of the present polypeptide, and Examples 14-1 to 14-6 below describe preferred embodiments of the present pharmaceutical composition for diseases susceptible to treatment with IFN-γ.

Example 13

Preparation of Polypeptide 13-1: Preparation of Polypeptide

The immunoreaction of newborn hamsters were suppressed in a conventional manner by injecting a rabbit antiserum to hamster antithymus into the hamsters, where their dorsal subcutaneous tissues were transplanted with about $5\times10^5$ cells/hamster of THP-1 cells (ATCC TIB202), a myelomonocytic cell line of a human acute leukemia, and the hamsters were fed for 3 weeks in a conventional manner. Tumor masses, which were about 15 g weight each and subcutaneously formed in each hamster were extracted, suspended in physiological saline in a conventional manner, and washed with PBS.

In accordance with the method by Matthew J. Kostura et al., *Proc. Natl. Acad. Sci. USA* 86:5227-5231 (1989), the suspended cells were washed with ten volumes of cold 20 mM HEPES buffer (pH 7.4) containing 10 mM potassium chloride, 1.5 mM magnesium chloride, 0.1 mM EDTA, allowed to stand in 3 volumes of a fresh preparation of the same buffer for 20 min under ice-chilled conditions, lyophilized at −80° C., and thawed to disrupt cells. The disrupted cells were centrifuged, and the supernatant was fed to a column packed with DEAE-SEPHAROSE, (a gel for ion-exchange chromatography commercialized by Pharmacia LKB Biotechnology AB, Uppsala, Sweden) previously equilibrated with 10 mM phosphate buffer (pH 6.6), followed by washing the column with 10 mM phosphate buffer (pH 6.6), and eluting with a sodium chloride concentration gradient from 0 M to 0.5 M, and collecting fractions eluting at about 0.2 M sodium chloride.

The collected fractions were pooled, dialyzed against 10 mM phosphate buffer (pH 6.8), fed to a column packed with DEAE 5PW (a gel for ion-exchange chromatography commercialized by Tosoh Corporation, Tokyo, Japan), which had been previously equilibrated with 10 mM phosphate buffer (pH 6.8), eluted with a linear concentration gradient of sodium chloride from 0 M to 0.5 M in 10 mM phosphate buffer (pH 6.8), and fractions eluting at about 0.2-0.3 M sodium chloride were collected.

The resulting fractions were pooled and dialyzed against PBS. The dialyzed solution was fed to a cylindrical plastic immunoaffinity chromatography column prepared by first packing a immunoaffinity gel containing a monoclonal antibody, which had been prepared according to the method disclosed in Japanese Patent Application No.58,240/95 (applied for by the present applicant), and washed with PBS. 100 mM glycine-HCl buffer (pH 2.5) was fed to the column to effect fractionation, followed by collecting eluate fractions containing a polypeptide which induces IFN-γ production by immunocompetent cells, dialyzing the fractions against sterile distilled water, concentrating the dialyzed solution with a membrane filter, and lyophilizing the concentrate to obtain a solid purified polypeptide. The yield was about 50 ng per hamster.

13-2: Preparation of Polypeptide

Dorsal subcutaneous tissues of newborn nude mice were injected with about $1\times10^6$ cells/nude mouse of KG-1 cells (ATCC CCL246), a myelomonocytic cell line derived from human acute myelomonocytic leukemia, and the mice were fed for 4 weeks in conventional manner. Tumor masses of about 20 g weight each, which were formed subcutaneously in each nude mouse, were extracted and dispersed in physiological saline in a conventional manner. The cells were washed and disrupted similarly as in Example 13-1, and the resulting mixture was purified to obtain a purified polypeptide which induces IFN-γ production by immunocompetent cells in a yield of about 20 ng per nude mouse.

The amino acid sequence of a portion of the purified polypeptide was analyzed in accordance with the method in Examples 9-11, revealing that the polypeptide has the partial amino acid sequence of SEQ ID NO:14 in the N-terminal region and a similar molecular weight and biological activity as the polypeptide in Example 8.

13-3: Preparation of Polypeptide

HL-60 cells (ATCC CCL240), a myelomonocytic cell line derived from human acute promyelocytic leukemia, were suspended in RPMI 1640 medium (pH 7.4), placed in an about 10-ml plastic cylindrical diffusion chamber in which a membrane filter with a diameter of 0.5 μm was installed, and the chamber was intraperitoneally embedded in an aged rat. The rat was fed for 4 weeks in a conventional manner, and then the chamber was removed. The propagated cells in the chamber were collected, washed with physiological saline, and disrupted similarly as in Example 13-1, followed by purifying the resulting mixture to obtain a purified polypeptide which induces IFN-γ production by immunocompetent cells. The yield was about 20 ng per rat.

The amino acid sequence of a portion of the purified polypeptide was analyzed in accordance with the method in Examples 9-11, revealing that the polypeptide has the partial amino acid sequence of SEQ ID NO:14 in the N-terminal region and has a similar molecular weight and biological activity to the polypeptide in Example 8.

13-4: Preparation of Polypeptide

THP-1 cells (ATCC TIB202), a myelomonocytic cell line derived from human acute monocytic leukemia, were suspended in RPMI 1640 medium (pH 7.2) supplemented with 10 v/v % fetal bovine serum to give a cell density of about $3\times10^5$ cells/ml, and cultured at 37° C. for 3 weeks in a 5 v/v % $CO_2$ incubator while replacing the medium with a fresh one. The propagated cells were separated from the resulting culture, washed with physiological saline, and disrupted similarly as in Example 13-1, followed by purifying the resulting mixture to obtain a purified polypeptide which induces IFN-γ production in a yield of about 10 ng per litter of the culture.

The amino acid sequence of a portion of the purified polypeptide was analyzed in accordance with the method in Examples 9-11, revealing that the polypeptide has the partial amino acid sequence of SEQ ID NO:14 in the N-terminal region and has a similar molecular weight and biological activity to the polypeptide in Example 8.

13-5: Preparation of Polypeptide

Dorsal subcutaneous tissues of newborn hamsters, immunosuppressed by injection of a rabbit antithymus serum in a conventional manner, were injected with about $5\times10^5$ cells/head of A253 cells (ATCC HTB41), a human epidermoid carcinoma from the submaxillary gland, and fed for 3 weeks in the usual manner. Thereafter, tumor masses of about 10 g weight in each hamster that were formed subcutaneously, were extracted, dispersed in physiological saline, and washed with PBS.

The propagated cells thus obtained were washed with 20 mM HEPES buffer (pH 7.4) containing 10 mM potassium chloride, 1.5 mM magnesium chloride, and 0.1 mM EDTA, and suspended in a fresh preparation of the same buffer to give a cell density of about $2\times10^7$ cells/ml. The suspended cells were disrupted with a homogenizer, centrifuged to remove cell debris and obtain a supernatant, followed by concentrating the supernatant with an ultrafiltration membrane to obtain a cell extract containing a polypeptide which induces IFN-γ production by immunocompetent cells. The extract was purified similarly as in the method of Example 13-1, concentrated, and lyophilized to obtain a solid purified polypeptide in a yield of about 3 μg per hamster.

The purified polypeptide was sampled and analyzed in accordance with the methods in Examples 9-11, revealing that it has the amino acid sequence of SEQ ID NO:14 in the N-terminal region and has a similar molecular weight and biological activities to those of the polypeptide in Example 8.

13-6: Preparation of Polypeptide

A seed culture of A-253 cells was inoculated into RPMI 1640 medium (pH 7.4) supplemented with 10 v/v % fetal calf serum and cultured in a conventional manner at 37° C. until a monolayer of cells was formed. Thereafter, the cells were detached from the surface of the culture vessel by using TRYPSIN-EDTA, a trypsin commercialized by Gibco BRL, Gaithersburg, Md., and washed with PBS. In accordance with the method in Example 13-1, the cells were disrupted, and the disrupted cells were centrifuged to obtain a supernatant which was then incubated at 37° C. for 6 hours, purified, concentrated, and lyophilized to obtain a solid purified polypeptide which induces IFN-γ production by immunocompetent cells in a yield of about 1 μg per $10^7$ cells. The supernatant was sampled and analyzed in accordance with the method in Example 9-11, revealing that the polypeptide has the amino acid sequence of SEQ ID NO:14 in the N-terminal region and has a similar molecular weight and biological activities to those of the polypeptide in Example 8.

13-7: Preparation of Polypeptide

A seed culture of A-253 cells was inoculated into RPMI 1640 medium (pH 7.4) supplemented with 10 v/v % fetal calf serum and cultured in a conventional manner at 37° C. until a monolayer of cells was formed. Thereafter, the culture medium was replaced with a serum-free RPMI 1640 medium (pH 7.4) supplemented with 10 IU/ml of a natural IFN-γ derived from KG-1 cells as an inducer, and incubated at 37° C. for 48 hours. The culture was centrifuged to obtain a supernatant which was then purified by the method in Example 13-1, concentrated, and lyophilized to obtain a solid purified polypeptide which induces IFN-γ production by immunocompetent cells in a yield of about 5 ng per $10^7$ cells.

The supernatant was sampled and analyzed in accordance with the method in Examples 9-11, revealing that the polypeptide has the amino acid sequence of SEQ ID NO:14 in the N-terminal region and has a similar molecular weight and biological activities to those of the polypeptide in Example 8.

13-8: Preparation of Polypeptide

A purified polypeptide obtained by the method in Example 13-1 was dissolved in an adequate amount of sterile distilled water, and the solution was fed to a column packed with ASAHIPAK® C4P-50 4E (a gel for high-performance liquid chromatography commercialized by Showa Denko K.K., Tokyo, Japan), which had been previously equilibrated with 0.1 v/v % aqueous trifluoroacetic acid, followed by washing the column with 0.1 v/v % aqueous trifluoroacetic acid and feeding to the column a linear gradient solution of acetonitrile increasing from 0 v/v % to 90 v/v % in a solution of a mixture trifluoroacetic acid and acetonitrile at a flow rate of 60 ml/hour. Fractions containing a polypeptide which induces IFN-γ production by immunocompetent cells were collected from the eluted fractions, pooled, neutralized with 1 M aqueous Tris solution (pH 11.2), and concentrated in a conventional manner, followed by removing acetonitrile from the resulting concentrate to obtain a concentrated polypeptide with a purity of at least 95% in a yield of about 10% by weight with respect to the material protein, d.s.b.

In accordance with the method in Example 9, the concentrated polypeptide was sampled and analyzed for molecular weight, resulting in a single protein band, which induces IFN-γ production, corresponding to a molecular weight of 18,400±1,000 daltons. The amino acid sequence of another fresh sample was analyzed in accordance with the method in Examples 10 and 11, revealing that it has the amino acid sequence of SEQ ID NO:15 and SEQ ID NO:14 in the C- and N-terminal regions, and more particularly, the amino acid sequence of SEQ ID NO:19. Furthermore, the polypeptide has the amino acid sequences of SEQ ID NOs:16 and 17 as internal fragments and exhibited a similar biological activity to the polypeptide of Example 8 even when concentrated at a relatively high level.

Example 14

Production Formulations 14-1: Liquid

A purified polypeptide obtained by the method in Example 13-1 was dissolved in physiological saline containing 1 w/v % human serum albumin as a stabilizer, followed by obtaining therefrom a sterile liquid solution. The product with a satisfactory stability can be used as an injection, collunarium or nebula to treat and/or prevent diseases susceptible to treatment with IFN-γ, such as malignant tumors, viral diseases, bacterial infections, and immunopathies.

14-2: Dried Injection

A purified polypeptide obtained by the method in Example 13-2 was dissolved in physiological saline containing 1 w/v % of a purified gelatin as a stabilizer, and the solution was filtered through a sterile filter in a conventional manner. The sterile solution was distributed to vials in 1 ml volume doses, and lyophilized, followed by sealing the caps of the vials.

The product with a satisfactory stability can be used to treat and/or prevent diseases susceptive to treatment with IFN-γ, such as malignant tumors, viral diseases, bacterial infections, and immunopathies.

14-3: Dry Injection

A solid pharmaceutical was prepared similarly as in Example 14-2 except that a purified polypeptide obtained by the method in Example 13-5 and TREHAOSE® (a crystalline trehalose powder commercialized by Hayashibara Co., Ltd., Okayama, Japan), as a stabilizer were used.

The product with a satisfactory stability can be advantageously used as a dry injection for treating and/or preventing malignant tumors, viral diseases, bacterial infections, and immunopathies.

14-4: Ointment

HI-BIS-WAKO 104, a carboxyvinylpolymer commercialized by Wako Pure Chemicals, Tokyo, Japan, and TREHAOSE®, a crystalline trehalose powder commercialized by Hayashibara Co., Ltd., Okayama, Japan, were dissolved in sterile distilled water in the amounts of 1.4 w/w % and 2.0 w/w %, respectively, and the solution was mixed to homogeneity with a purified polypeptide obtained by the method in Example 13-3 and adjusted to pH 7.2 to obtain a paste containing about 1 mg of a purified polypeptide per g of the paste.

The product with a satisfactory spreadability and stability can be used to treat and/or prevent susceptive diseases such as malignant tumors, viral diseases, bacterial infections, and immunopathies.

14-5: Tablet

A purified polypeptide, obtained by the method in Example 13-4, and LUMIN (4,4'[3-[2-(1-ethyl-4-(1H)-quinolinylidene)ethylidene]propenylene]bis(1-ethylquinolinium iodide) as a cell activator were mixed to homogeneity with FINETOSE®, an anhydrous crystalline α-maltose powder commercialized by Hayashibara Co., Ltd., Okayama, Japan, and the mixture was tableted in a conventional manner to obtain tablets of about 200 mg weight each, which contain the purified polypeptide and LUMIN in an amount of about 1 mg each.

The product with a satisfactory allowability, stability and cell-activating activity can be used to treat and/or prevent susceptive diseases such as malignant tumors, viral diseases, microbism, and immunopathies.

14-6: Agent for Adoptive Immunotherapy

Human monocytes were separated from the peripheral blood of a patient with malignant lymphoma, and suspended in RPMI 1640 medium (pH 7.2), which had been supplemented with 10 v/v % human AB serum and preheated at 37° C., to give a cell density of about $1 \times 10^6$ cells/ml. The cell suspension was mixed with about 10 ng/ml of a purified polypeptide obtained by the method in Example 13-1 and about 100 units/ml of a recombinant human interleukin 2, and incubated at 37° C. for 1 week, followed by centrifugation to collect LAK cells.

LAK cells exerted a strong cytotoxic effect on lymphoma cells when introduced into the patient, and the therapeutic effect is significantly higher than that of the conventional adoptive immunotherapy using interleukin 2 alone. Cytotoxic T-cells, obtained by treating a patient's tumor tissue invasive-lymphocytes instead of the patient's monocytes, showed an effect similar to LAK cells when reintroduced into the patient. The agent for adoptive immunotherapy can be suitably applied to solid tumors such as malignant nephroma, malignant melanoma, large intestinal cancer, and lung cancer.

Example 15

Preparation of Polypeptide

15-1: Preparation of Transformant KGFHH2

To a 0.5-ml reaction tube were added 8 µl of 25 mM magnesium chloride, 10 µl of 10×PCR buffer, 1 µl of 25 mM dNTP mix, 1 µl of 2.5 units/µl of AmpliTaq DNA polymerase, 1 ng of a recombinant DNA containing the nucleotide sequence of SEQ ID NO:5 prepared from a phage DNA clone by the method in Japanese Patent Application No.304,203/94 and disclosed above in Example 5 and containing a DNA encoding the polypeptide of SEQ ID NO:6, and an adequate amount of a sense primer and an antisense primer represented by 5'-ATAGAATTCAAATG-TACTTTGGCAAGCTTGAATC-3' (SEQ ID NO:21), chemically synthesized based on an amino acid sequence near the N- and C-termini of SEQ ID NO:6, and 5'-ATAAAGCTTCTAGTCTTCGTTTTGAAC-3' (SEQ ID NO:22), and sterilized distilled water was added to give a total volume of 100 µl. The reaction mixture solution was successively incubated at 94° C. for 1 min, at 43° C. for 1 min, and at 72° C. for 1 min, and this sequential incubation was repeated 3 times. The resultant mixture was further successively incubated at 94° C. for 1 min, at 6020 C. for 1 min, and at 72° C. for 1 min, and this sequential incubation was repeated 40 times to effect PCR amplification.

The resultant PCR reaction mixture and pCR-Script SK (+), a plasmid vector commercialized by Stratagene Cloning Systems, La Jolla, Calif., USA, were ligated using DNA ligase to obtain a recombinant DNA which was then introduced into competent host cells of *Escherichia coli* XL-1 Blue MRF'Kan, a microorganism commercialized by Stratagene Cloning Systems, Calif., USA, to transform the host cells. The transformant thus obtained was inoculated into L-broth (pH 7.2) containing 50 µg/ml ampicillin, and cultured at 37° C. for 18 hours under shaking conditions (aeration), followed by centrifuging the resultant culture to collect the proliferated transformants and isolating recombinant DNAs using a conventional alkaline-SDS method. A part of the recombinant DNAs was analyzed by the dideoxy sequencing method and found to contain a DNA which has EcoRI and HindIII cleavage sites at the 5'- and 3'-termini of SEQ ID NO:5, a methionine codon which initiates polypeptide synthesis, positions in the sites corresponding to those before and after the N- and C-termini of SEQ ID NO:5, and a TAG codon which terminates polypeptide synthesis.

Figure 4:
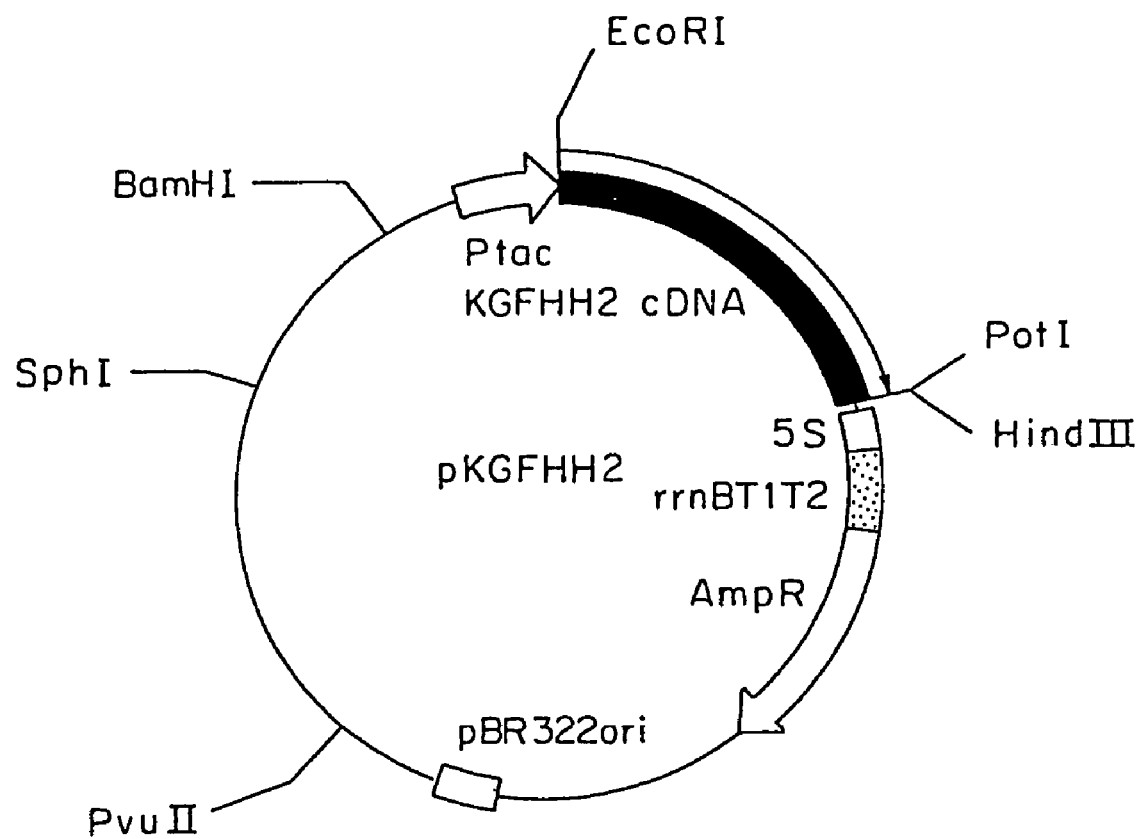
FIG. 4 is a schematic representation of the structure of recombinant plasmid pKGFHH2, where KGFHH2 cDNA represents the cDNA encoding the INF-γ inducing polypeptide, Ptac represents the tac promoter, rrnBT1T2 represents a terminator of a ribosomal RNA operon, AmpR represents ampicillin resistance gene, and pBR322 ori represents an *Escherichia coli* replication initiation site.

The remaining recombinant DNAs were cleaved with restriction enzymes EcoRI and HindIII, and 0.1 µg of the resultant EcoRI-HindIII DNA fragment obtained with DNA LIGATION KIT Version 2 (a DNA ligation kit commercialized by Takara Shuzo Co., Ltd., Tokyo, Japan), and 10 ng of pKK223-3 (a plasmid vector commercialized by Pharmacia LKB Biotechnology AB Uppsala, Sweden) which had been previously cleaved with the above restriction enzymes, were ligated by incubating them at 16° C. for 30 min to obtain a replicable recombinant pKGFHH2 DNA. By using a competent cell method, *Escherichia coli* Y1090 strain (ATCC 37197) was transformed with replicable recombinant DNA pKGFHH2, and the transformant generated, KGFHH2 was inoculated into L-broth (pH 7.2) containing 50 µ/ml ampicillin, and incubated at 37° C. for 18 hours under shaking conditions. The resultant culture was centrifuged to collect the proliferated transformants, a portion of which was treated by a conventional alkaline-SDS method to extract the recombinant DNA pKGFHH2. As shown in FIG. 4, the analysis by the dideoxy method revealed that, in recombinant pKGFHH2 DNA, the KGFHH2 CDNA which contains the nucleotide sequence of SEQ ID NO:5, was ligated downstream of a Tac promoter.

15-2: Production and Purification of Polypeptide from Transformant KGFHH2

An L-broth (pH 7.2) containing 50 µg/ml of ampicillin was sterilized by autoclaving, cooled to 37° C., inoculated with the transformant KGFHH2 prepared above, and incubated at the same temperature for 18 hours under shaking conditions to obtain a seed culture. Eighteen liters of a fresh preparation of the same L-broth was placed in a 20-L jar fermenter, sterilized similarly as above, cooled to 37° C., inoculated with 1 v/v % of the seed culture, and cultured at the same temperature for 8 hours under aeration and agitation conditions. The resultant culture was centrifuged to collect cells, and the cells were then suspended in a mixture solution (pH 7.3) consisting of 150 mM sodium chloride, 16 mM disodium hydrogen phosphate, and 4 mM sodium dihydrogen phosphate, disrupted with ultrasound, and centrifuged to remove cell debris and obtain a supernatant.

Ammonium sulfate was added to the supernatant to give a concentration of 40 w/v % and dissolved to homogeneity. The ammonium sulfate solution was centrifuged to obtain a supernatant, which was then fed to a column packed with PHENYL SEPHAROSE (a product of Pharmacia LKB Biotechnology AB, Uppsala, Sweden), which had been previously equilibrated with 10 mM phosphate buffer (pH 6.6) containing 1.5 M ammonium sulfate, followed by washing the column with a fresh preparation of the same buffer, and feeding a gradient buffer of ammonium sulfate ranging from 1.5 M to 0 M in 10 mM phosphate buffer (pH 6.6) to the column.

A gel for immunoaffinity chromatography was prepared and packed in a plastic cylindrical column which was then washed with PBS, fed with 10 ml of fractions eluted from the above PHENYL SEPHAROSE column at about 1.0 M ammonium sulfate, washed with a fresh preparation of the same PBS, and fed with 0.1 M glycine-HCl buffer (pH 2.5) containing 1 M sodium chloride, followed by collecting fractions with IFN-γ inducibility. The fractions were pooled, dialyzed against PBS at 4° C. overnight, and concentrated, followed by assaying the resultant concentrate for IFN-γ inducibility and protein content, which revealed that the purification procedure yielded about 25 mg of the polypeptide with a purity of at least 95% per L of the culture.

Analysis further revealed that the purified polypeptide has the following physicochemical properties:

(1) when electrophoresed on SDS-PAGE under non-reducing conditions, the purified polypeptide appeared as a main polypeptide band having IFN-γ inducibility at a position corresponding to 18,500±3,000 daltons;

(2) a pI of 4.9±1.0 on chromatofocusing; and (3) the amino acid sequence containing N-terminus of the purified polypeptide had the amino acid sequence of SEQ ID NO:20 which was the same as the N-terminal sequence of SEQ ID NO:6 except that methionine was added at the N-terminus.

Example 16

Biological Activity 16-1: Production of IFN-γ by Immunocompetent Cell

Fresh blood was collected from healthy volunteers using heparinized syringes, and diluted two-fold with serum-free RPMI 1640 medium (pH 7.4). The diluted blood was overlaid onto FICOLL and centrifuged to obtain lymphocytes which were then washed with RPMI 1640 medium (pH 7.4) supplemented with 10 v/v % fetal calf serum, and suspended in a fresh preparation of the same medium to give a cell density of $5 \times 10^6$ cells/ml. The cell suspension was distributed to 96-well microplates in an amount of 0.15 ml/well.

A polypeptide obtained by the method in Example 15 was diluted to give an appropriate concentration with RPMI 1640 medium (pH 7.4) supplemented with 10 v/v % fetal calf serum. The diluted solution was distributed to the microplates in an amount of 0.05 ml/well, followed by adding 0.05 ml/well of a fresh preparation of the same medium supplemented with or without 2.5 µg/ml of concanavalin A or 50 units/ml of a recombinant human interleukin 2 to the microplates, and then incubating the microplates at 37° C. for 24 hours in an incubator under 5 v/v % $CO_2$ conditions. After cultivation, 0.1 ml of culture supernatant in each well was sampled and assayed for IFN-γ content with a conventional enzyme immunoassay. As a control, a system free of the polypeptide was provided, and treated similarly as above. The results are presented in Table 6. The IFN-γ content data shown in Table 6 was calibrated using Gg23-901-530, an International Standard for Interferon, Human(HuIFN-γ), obtained from National Institutes of Health, Bethesda, Md., USA, and expressed by international units (IU).

TABLE 6

| | IFN-γ productivity (IU/ml) | | |
|---|---|---|---|
| Polypeptide concentration (ng/ml) | Polypeptide plus | Polypeptide plus 0.5 µg/ml of concanavalin A | Polypeptide 10 U/ml of interleukin 2 |
| 0 | 0 | 0 | 0 |
| 1.6 | 1 ± 2 | 92 ± 32 | 184 ± 12 |
| 8.0 | 3 ± 1 | 220 ± 21 | 397 ± 31 |
| 40.0 | 6 ± 4 | 380 ± 34 | 526 ± 28 |
| 200.0 | 14 ± 6 | 549 ± 105 | 637 ± 99 |

The results in Table 6 show that lymphocytes as immunocompetent cell produced IFN-γ in response to the action of the polypeptide of the present invention. As evident from the results, the use of the polypeptide in combination with interleukin 2 or concanavalin A as a cofactor enhanced IFN-γ production.

16-2: Enhancement of Cytotoxicity by NK Cell

Fresh blood was collected from healthy volunteers using heparinized syringes, and diluted two-fold with 10 mM phosphate buffer (pH 7.4) containing 140 mM sodium chloride. The collected blood was overlaid onto FICOLL, centrifuged, and then further subjected to FICOLL gradient centrifugation to obtain high-density lymphocytes.

The lymphocytes were suspended in RPMI 1640 medium (pH 7.2) containing 10 µg/ml kanamycin, $5 \times 10^{-5}$ M 2-mercaptoethanol, and 10 v/v % fetal calf serum to give a cell density of $1 \times 10^6$ cells/ml. The cell suspension was distributed into 12-well microplates in an amount of 0.5 ml/well. A polypeptide obtained by the method in Example 15 was appropriately diluted with a fresh preparation of the same medium, and the diluted solution was distributed to the microplates in an amount of 1.5 ml/well, followed by distributing 0.5 ml/well of a fresh preparation of the same medium with or without 50 units/ml of a recombinant human interleukin 2. The microplates were incubated in an incubator at 37° C. for 24 hours under 5 v/v % $CO_2$ conditions, followed by washing with 10 mM phosphate buffer (pH 7.4) containing 140 mM sodium chloride to obtain cultured lymphocytes containing NK cells as effector cells. K-562 cells (ATCC CCL 243), derived from human chronic myelogenous leukemia, as NK cell-sensitive target cells labelled in the usual manner with $^{51}Cr$, were distributed to 96-well microplates to give $1\times10^4$ cells/well. Effector cells were added to each well in the ratio (effector cells):(target cells) of 2.5:1, 5:1 or 10:1, and incubated in an incubator at 37° C. for 4 hours under 5 v/v % $CO_2$ conditions. According to what is conventionally done, the radioactivity of each supernatant in each well was measured to count the dead target cells. In each system, the percentage (%) of dead target cells to target cells was calculated to determine the cytotoxicity level. The results are presented in Table 7.

TABLE 7

| Concentration of polypeptide (pM) | Concentration of interleukin 2 (unit/ml) | Cytotoxicity (%) (Effector cell):(Target cell) | | |
|---|---|---|---|---|
| | | 2.5:1 | 5:1 | 10:1 |
| 0 | 0 | 22 | 35 | 65 |
| 0 | 10 | 30 | 48 | 73 |
| 0.5 | 0 | 23 | 36 | 66 |
| 0.5 | 10 | 32 | 50 | 75 |
| 5 | 0 | 25 | 39 | 68 |
| 5 | 10 | 35 | 52 | 78 |
| 50 | 0 | 29 | 47 | 73 |
| 50 | 10 | 41 | 59 | 85 |
| 500 | 0 | 37 | 50 | 83 |
| 500 | 10 | 52 | 70 | 93 |

Note:
In the Table, (pM) means $10^{-12}$ M.

The results in Table 7 show that the polypeptide has an activity of enhancing the cytotoxicity by NK cells. As also shown in Table 7, the presence of interleukin 2 further enhances cytotoxicity.

16-3: Induction of LAK Cell Formation

According to what is conventionally done, $^{51}Cr$-labelled Raji cells (ATCC CCL 86), derived from human Burkitt lymphoma as a target cell resistant to NK cells, were placed in 96-well microplates to give $1\times10^4$ cells/well, and cultured for 72 hours. Cultured lymphocytes, containing LAK cells as effector cells prepared similarly as above, and target cells were added to the microplates in the ratio of 5:1, 10:1 or 20:1, and the microplates were incubated in an incubator at 37° C. for 4 hours under 5 v/v % $CO_2$ conditions. Thereafter, the radioactivity of each supernatant in each well was measured, and the cytotoxicity (%) was calculated similarly as above. The results are presented in Table 8.

TABLE 8

| Concentration of polypeptide (pM) | Concentration of interleukin 2 (unit/ml) | Cytotoxicity (%) (Effector cell):(Target cell) | | |
|---|---|---|---|---|
| | | 5:1 | 10:1 | 20:1 |
| 0 | 0 | 11 | 21 | 34 |
| 0 | 10 | 15 | 28 | 38 |
| 0.5 | 0 | 13 | 22 | 35 |
| 0.5 | 10 | 17 | 31 | 43 |
| 5 | 0 | 15 | 23 | 39 |
| 5 | 10 | 19 | 34 | 48 |
| 50 | 0 | 20 | 25 | 44 |
| 50 | 10 | 23 | 42 | 54 |
| 500 | 0 | 27 | 34 | 57 |
| 500 | 10 | 31 | 54 | 67 |

Note:
In the Table, (pM) means $10^{-12}$ M.

The results in Table 8 show that the present polypeptide has an activity of inducing LAK cells. As is shown in the results, the presence of interleukin 2 further enhances the induction.

Example 17

Acute Toxicity Test

According to what is done conventionally, a purified polypeptide obtained by the method in Example 15 was percutaneously, perorally or intraperitoneally administered to 8-week-old mice. As a result, the $LD_{50}$ of the purified polypeptide was about-1 mg/kg or higher, independent of the route of administration. This provides evidence that the polypeptide according to the present invention can be safely incorporated into pharmaceuticals for administration to humans.

Example 18

Production Formulations 18-1: Solution

A polypeptide obtained by the method in Example 15, was dissolved in physiological saline containing 1 w/v % human serum albumin as a stabilizer to obtain a 1 mg/ml polypeptide solution which was then sterilized by membrane filter to obtain a solution. The resultant product with a satisfactory stability can be used in the treatment and/or the prevention of diseases susceptible to treatment with IFN-γ, such as malignant tumors, viral diseases, bacterial infectious diseases, and immune diseases.

18-2: Dry Injection

A polypeptide obtained by the method in Example 15, was dissolved in 100 ml physiological saline containing 1 w/v % purified gelatin as a stabilizer, and the solution was sterilized with a membrane filter in the usual manner. One ml aliquot doses of the sterilized solution were distributed to vials, lyophilized, and cap sealed. The product with a satisfactory stability can be used as a dry injection for treating and/or preventing diseases susceptible to treatment with IFN-γ, such as malignant tumors, viral diseases, bacterial diseases, and immune diseases.

18-3: Ointment

HI-BIS-WAKO 104, a carboxyvinylpolymer commercialized by Wako Pure Chemicals, Tokyo, Japan, and a purified trehalose were dissolved in distilled water to give concentrations of 1.4 w/w % and 2.0 w/w %, respectively, in a solution. A polypeptide obtained by the method in Example 15 was then dissolved to homogeneity in the solution, followed by adjusting the pH of the resultant solution to pH 7.2 to obtain a paste containing about 1 mg/g of the polypeptide. The product with a satisfactory spreadability and stability can be used as an ointment for treating and/or preventing diseases susceptible to treatment with IFN-γ, such as malignant tumors, viral diseases, bacterial infectious diseases, and immune diseases.

18-4: Tablet

A polypeptide obtained by the method in Example 15, and LUMIN, i.e., [4,4'-[3-[2-(1-ethyl-4(1H)-quinolinylidene) ethylidene]propenylene]bis(1-ethylquinolinium iodide, as a cell activator were mixed to homogeneity with FINE-TOSE®, an anhydrous crystalline α-maltose commercialized by Hayashibara Co., Ltd., Okayama, Japan, and the mixture was tableted in the usual manner by a tableting machine to obtain tablets of about 200 mg weight each which contain the polypeptide and LUMIN at about 1 mg each. The product having a satisfactory swallowing ability, stability, and cell activating activity, can be used as a tablet for treating and/or preventing diseases susceptive to treatment with IFN-γ, such as malignant tumors, viral diseases, bacterial infectious diseases, and immune diseases.

Example 19

Adoptive Immunotherapeutic Agent

Mononuclear cells were isolated from the peripheral blood of a patient with malignant lymphoma, suspended in a RPMI 1640 medium (pH 7.2) supplemented with 10 v/v % human AB serum, and preheated to 37° C. to give a cell density of about 1×10⁶ cells/ml. The cells were mixed with about 1.0 μg/ml of a polypeptide obtained by the method in Example 15, and about 100 units/ml of a recombinant human interleukin 2, followed by incubating in a 5 v/v % $CO_2$ incubator at 37° C. for 1 week, and centrifuging the resultant culture to collect LAK cells.

The LAK cells thus obtained exhibited a strong cytotoxicity on lymphoma cells when introduced into the donor patient, and exerted a higher cytotoxicity than that attained by the adoptive immunotherapy using interleukin 2 alone. Cytotoxic T-cells obtained by similarly treating lymphocytes which invaded into the tumor tissues of the patient, were injected into the donor patient in place of the above lymphocytes and resulted in exertion of a similar effect as in LAK cells. The adoptive immunotherapeutic agent can be arbitrarily used to treat solid malignant tumors, such as renal cancer, malignant melanoma, colonic cancer, rectal cancer, and lung cancer.

Example 20

Preparation of Hybridoma H-1

Transformant KGFHH2 was generated as described in Example 15. Polypeptides produced in culture from this transformant were centrifuged in ammonium sulfate and the supernatant was fractionated by elution on a PHENYL SEPHAROSE column as described in Example 15.

Fractions eluted at around 1.0 M ammonium sulfate from the PHENYL SEPHAROSE column were pooled, membrane filtered, dialyzed against 10 mM phosphate buffer (pH 6.5) at 4° C. for 18 hours, and fed to a column packed with DEAE 5PW (a product commercialized by Tosoh Corporation, Tokyo, Japan), which had been previously equilibrated with 10 mM phosphate buffer (pH 6.5), followed by washing the column with a fresh preparation of the same buffer, and feeding a linear gradient buffer of sodium chloride ranging from 0 M to 0.2 M in 10 mM phosphate buffer (pH 6.5) to the column while collecting fractions eluting at 0.05 M sodium chloride.

Thereafter, the fractions were concentrated with a membrane and fed to a column packed with SUPERDEX 75 (a product of Pharmacia LKB biotechnology AB, Uppsala, Sweden), which had been equilibrated with phosphate buffered saline, followed by feeding a fresh preparation of PBS to the column to collect fractions corresponding to about 18,500 daltons. An aqueous solution containing about 5.2 mg of a purified protein was obtained with the total yield throughout the purification being about 10%.

Analysis according to Example 15 revealed that the purified polypeptide appeared as a main protein band having an IFN-γ inducibility at a position corresponding to 18,500±3,000 daltons when electrophoresed in SDS-PAGE under reducing conditions, and had a pI of 4.9±1.0 on chromato focusing. The amino acid sequence containing the N-terminus of the purified protein was also determined to have the amino acid sequence of SEQ ID NO:20, which corresponds to the N-terminal sequence of SEQ ID NO:6 with a methionine added to its N-terminus.

Ten-week-old BALB/c mice were each intraperitoneally injected with 20 μg of a purified polypeptide, obtained above from the transformant KGFHH2 in combination with a complete Freund's adjuvant. The mice were further intraperitoneally injected twice with the same dose at an interval of two weeks with an intravenous injection of the same dose 1 week after the final intraperitoneal injection. The splenocytes were prepared from the mice and suspended to obtain a cell suspension.

The spleen cells and SP2/O-Ag14 cells from mouse myeloma cells (ATCC CRL 1581) were suspended in RPMI 1640 medium (pH 7.2) preheated to 37° C. at cell densities of 3×10⁴ cells/ml and 1×10⁴ cells/ml, respectively, and centrifuged to collect sediment. One ml of a serum-free RPMI 1640 medium (pH 7.2) containing 50 w/v % polyethylene glycol with an average molecular weight of 1,500 daltons was added dropwise to the precipitate over 1 min. The mixture was incubated at 37° C. for 1 min, followed by adding a serum-free RPMI 1640 medium (pH 7.2) dropwise to the mixture to bring the volume up to 50 ml, centrifuging the mixture, and collecting the sediment formed. The sediment thus obtained was suspended in HAT medium, hdistributed to 96-well microplates in an amount of 200 μl/well, and incubated at 37° C., for 1 week, followed by selecting for hybridomas.

The amount of antibodies secreted in the supernatant in each well was assayed on enzyme immunoassay based on the immunoreaction of the antibodies and purified polypeptide obtained above from the transformant KGFHH2. Hybridomas capable of producing antibodies which strongly reacted with the purified polypeptide were selected. A cloned hybridoma H-1 cell capable of producing the present monoclonal antibody was obtained in the usual manner by repeatedly treating these hybridomas with limiting dilution.

Example 21

Preparation of Monoclonal Antibody H-1mAb and its Analysis on Western Blot Technique 21-1: Preparation of Monoclonal Antibody H-1mAb Hybridoma H-1 cells obtained in Example 20 were suspended in RPMI 1640 medium (pH 7.2) supplemented with 5 v/v % calf serum to give a cell density of about 1×10⁶ cells/ml, and incubated in an incubator at 37° C., under 5 v/v % CO$_2$ conditions while scaling up the culture. When the cell density of the culture reached a prescribed level, 1×10⁷ cells/mouse of the proliferated hybridoma H-1 cells were intraperitoneally injected into 8 week old BALB/c mice, which had been intraperitoneally injected previously with 0.5 ml/mouse of pristane, followed by feeding the mice in the usual manner for one week.

Ascites were collected from the mice, diluted three-fold with PBS, mixed with ammonium sulfate to give a saturation degree of 50 w/v %, allowed to stand at 4° C. for 24 hours, and centrifuged to collect sediment. The collected sediment was dialyzed against an aqueous solution of 20 mM potassium dihydrogen phosphate (pH 6.7) at 4° C. overnight, and fed to a column of hydroxyapatite which had been previously equilibrated with a fresh preparation of the same aqueous solution, followed by feeding to the column a linear gradient of a potassium dihydrogen phosphate buffer (pH 6.7) ranging from 20 mM to 300 mM to obtain an aqueous solution containing the present monoclonal antibody H-1mAb. The yield was about 5 mg per mouse. Conventional analysis revealed that the antibody belongs to the IgG$_1$ class.

21-2: Analysis on Western Blot Technique

One µg of the purified polypeptide obtained in Example 15-2 was added to a solution containing 100 mg dithiothreitol, 0.5 ml of an aqueous solution of 10 w/v % SDS, and 1 ml of glycerol, and the mixture was incubated at 37° C. for 1 hour and electrophoresed on SDS-PAGE. The polypeptide on the gel was transferred to a nitrocellulose membrane in the usual manner and the nitrocellulose membrane was then soaked in a culture supernatant of hybridoma H-1 cells for 1 hour, and washed with 50 mM Tris-HCl buffer (pH 7.5) containing 0.05 v/v % TWEEN 20 to remove excessive amounts of antibodies. The membrane was further soaked for 1 hour in PBS containing an anti-mouse Ig antibody prepared from rabbits to effect an immunoreaction, washed with 50 mM Tris-HCl buffer (pH 7.5) containing 0.05 v/v % TWEEN 20, and soaked in 50 mM Tris-HCl buffer (pH 7.5) containing 0.005 v/v % hydrogen peroxide and 0.3 mg/ml 3,3'-diaminobenzidine to provide a change in color.

As a control, a system using a recombinant human interleukin 12 in place of the purified polypeptide was provided, and treated similar to the purified polypeptide above. Calf serum albumin (MW=67,000 daltons), ovalbumin (MW=45,000 daltons), carbonic anhydrase (MW=30,000 daltons), trypsin inhibitor (MW=20,100 daltons), and α-lactalbumin (MW=14,400 daltons) were used as marker proteins. The results are shown in FIG. 5.

Figure 5:
FIG. 5 is an image of a Western blot showing the reactivity of the present purified polypeptide and human interleukin 12 with the monoclonal antibody H-1mAb.
Figure 5:
Figure 5:
Figure 5:
Figure 5:
Figure 5:

As is evident from FIG. 5, the monoclonal antibody H-1mAb specifically reacted with the purified polypeptide (lane 1) obtained in Example 15-2, but did not react with human interleukin 12 (lane 2). This demonstrates that the present monoclonal antibody reacts specifically and not non-specifically to the polypeptide obtained in Example 15-2.

Example 22

Preparation of Hybridoma H-2 and Monoclonal Antibody H-2mAb

Hybridoma H-2, which produces a monoclonal antibody H-2, was prepared similarly as in Example 21, except that P3-X63-Ag8 cells (ATCC TIB9) were used in place of SP/0-14Ag cells. Hybridoma H-2 was proliferated similarly as in Example 21, and about 5.6 mg of monoclonal antibody H-2mAb per BALB/c mouse was purified from the ascites. Conventional analysis revealed that the monoclonal antibody belongs to the IgM class, and it specifically reacted with the polypeptide purified in Example 15-2 when analyzed on Western blots as similarly done in Example 21.

Example 23

Purification of Polypeptide on Immunoaffinity Chromatography

Eighty mg of monoclonal antibody H-1mAb obtained in Example 21-1 was weighed and dialyzed against 0.1 M borate buffer (pH 8.5) containing 0.5 M sodium chloride at 4° C. overnight. Four g of CNBr-activated SEPHAROSE 4B (a water-insoluble carrier commercialized by Pharmacia LKB Biotechnology AB, Uppsala, Sweden) was swelled with 1 mM of an aqueous chloric acid solution, successively washed with a fresh preparation of the same buffer and 0.1 M borate buffer (pH 8.5) containing 0.5 M sodium chloride, admixed with about 10 ml of the aqueous monoclonal antibody solution obtained above, and successively incubated at ambient temperature and at 4° C. overnight under gentle stirring conditions. Thereafter, the resultant gel was successively washed with 1 M aqueous ethanolamine solution (pH 8.0), 0.1 M borate buffer (pH 8.5) containing 0.5 M sodium chloride, and 0.1 M acetate buffer (pH 4.0), and these washing steps were repeated five times. Finally, the gel was washed with PBS to provide a gel for immunoaffinity chromatography. Conventional analysis revealed that about 6 mg monoclonal antibody H-1mAb was linked to 1 ml of the gel.

Ten ml of the gel for immunoaffinity chromatography was packed in a plastic cylindrical.column, washed with PBS, and fed with 10 ml of a PHENYL SEPHAROSE eluted fraction containing about 0.1 mg/ml of the polypeptide purified in Example 15-2. The column was washed with a fresh preparation of PBS, and fed with 0.1 M glycine-HCl buffer (pH 2.5) containing 1 M sodium chloride to collect fractions with an IFN-γ inducing activity. The fractions were pooled, dialyzed against PBS at 4° C. overnight, concentrated and assayed the IFN-γ inducing activity and protein content, revealing that this purification procedure yielded a purified polypeptide with a purity of 95 w/w % or higher in a yield of about 100%.

Example 24

Detection of Polypeptide on Enzyme Immunoassay

Rabbits were immunized in the usual manner with a purified polypeptide obtained in Example 15-2, and their blood was later collected. Immunoglobulin G antibody was isolated from the blood, dissolved in PBS to give a concentration of 20 µg/ml, and the solution was distributed into 96-well microplates in an amount of 100 µl/well. The microplates were incubated at ambient temperature for 3 hours, followed by removing solutions containing IgG from the microplates, adding PBS containing 1 w/v % calf serum albumin to the microplates in an amount of 200 µl/well, and allowing them to stand at 4° C. overnight.

Phosphate buffered saline was removed from the microplates and the microplates were then washed with PBS containing 0.05 v/v % TWEEN 20, and poured with 100 µl/well of a solution prepared by appropriately diluting the polypeptide with PBS containing 0.5 w/v % calf serum albumin, followed by reacting the mixture solution at ambient temperature for 2 hours under shaking conditions. The microplates were washed with PBS containing 0.05 v/v % TWEEN 20, and 100 µl/well of a solution containing a monoclonal antibody H-1mAb labelled with biotin was added, followed by reacting the solution at ambient temperature for 2 hours under shaking conditions, washing the microplates with PBS containing 0.05 v/v % TWEEN 20, adding 100 µl/well of a solution containing a complex of horseradish peroxidase and streptoavidin, and further reacting the resultant mixture at ambient temperature for 2 hours under shaking conditions. The microplates were then washed with PBS containing 0.05 v/v % TWEEN 20, and the activity of the horseradish peroxidase linked to the purified polypeptide was measured for absorbance at a wavelength of 492 nm using o-phenylenediamine as substrate. The results are shown in Table 9.

TABLE 9

| Concentration of polypeptide (pg/ml) | Absorbance at 492 nm* | Relative error (%) |
|---|---|---|
| 1,000 | 1.51 ± 0.05 | 3.3 |
| 500 | 0.93 ± 0.05 | 5.4 |
| 250 | 0.55 ± 0.03 | 5.5 |
| 100 | 0.25 ± 0.02 | 8.0 |
| 50 | 0.137 ± 0.007 | 5.1 |
| 25 | 0.080 ± 0.007 | 8.8 |
| 0 | 0.024 ± 0.007 | — |

Note:
The symbol * means a statistical value of triplet.

As evident from the results in Table 9, the detection method according to the present invention accurately assays the polypeptide in an amount in the range of about 50-1,000 pg/ml.

Example 25

Detection of Polypeptide on Radioimmunoassay

Rabbits were immunized with the polypeptide purified in Example 15-2 in the usual manner, and their blood was later collected, followed by isolating an IgG antibody. The antibody was adsorbed onto polystyrene beads for radioimmunoassay in the usual manner, and allowed to stand in PBS containing 2 w/v % calf serum albumin at 4° C. overnight to obtain an immobilized antibody.

One polystyrene bead with the antibody adsorbed thereto was placed in a test tube, soaked in 0.2 ml of a solution prepared by diluting the purified polypeptide of Example 20 with PBS containing 0.5 w/v % calf serum albumin, and allowed to stand at 4° C. for 4 hours. The bead was then washed with PBS containing 0.05 v/v % TWEEN 20 and 0.5 w/v % calf serum albumin, soaked in 0.2 ml ($1\times10^5$ cpm) of a solution containing monoclonal antibody H-2mAb obtained in Example 22, labelled with $^{125}$I in the usual manner, and allowed to stand at 4° C. overnight. After removing an excessive amount of $^{125}$I-labelled antibody, the bead was washed with PBS containing 0.05 v/v % TWEEN 20 and 0.5 w/v % calf serum albumin, followed by counting the radioactivity of the bead on a gamma-counter. The results are shown in Table 10.

TABLE 10

| Concentration of polypeptide (pg/ml) | Count* (cpm) | Relative error (%) |
|---|---|---|
| 1,000.0 | 6,900 ± 200 | 2.9 |
| 500.0 | 4,100 ± 20 | 0.5 |
| 250.0 | 2,390 ± 50 | 2.1 |
| 125.0 | 1,590 ± 70 | 4.4 |
| 62.5 | 880 ± 10 | 1.1 |
| 0 | 700 ± 20 | — |

Note:
The symbol * means a statistical value of triplet.

As evident from the results in Table 10, the present detection method accurately assays for the polypeptide in the range of about 100-1,000 pg/ml.

While there has been described what is at present considered to be the preferred embodiments of the invention, it will be understood the various modifications may be made therein, and it is intended to cover in the appended claims all such modifications as fall within the true spirit and scope of the invention.

What is claimed is:

1. A monoclonal antibody which binds to the polypeptide of SEQ ID NO:8.

* * * * *

SEQUENCE LISTING

```
<160> NUMBER OF SEQ ID NOS: 22

<210> SEQ ID NO 1
<211> LENGTH: 25
<212> TYPE: PRT
<213> ORGANISM: Mus sp.

<400> SEQUENCE: 1

Ile Ile Ser Phe Glu Glu Met Asp Pro Pro Glu Asn Ile Asp Asp Ile
1               5                   10                  15

Gln Ser Asp Leu Ile Phe Phe Gln Lys
            20                  25

<210> SEQ ID NO 2
<211> LENGTH: 18
<212> TYPE: PRT
<213> ORGANISM: Mus sp.
```

<400> SEQUENCE: 2

Gln Pro Val Phe Glu Asp Met Thr Asp Ile Asp Gln Ser Ala Ser Glu
1               5                   10                  15

Pro Gln

<210> SEQ ID NO 3
<211> LENGTH: 471
<212> TYPE: DNA
<213> ORGANISM: Mus sp.
<220> FEATURE:
<221> NAME/KEY: CDS
<222> LOCATION: (1)..(471)
<223> OTHER INFORMATION: Xaa is methionine or threonine

<400> SEQUENCE: 3

| aac ttt ggc cga ctt cac tgt aca acc gca gta ata cgg aat ata aat | 48 |
|---|---|
| Asn Phe Gly Arg Leu His Cys Thr Thr Ala Val Ile Arg Asn Ile Asn | |
| 1               5                   10                  15 | |

| gac caa gtt ctc ttc gtt gac aaa aga cag cct gtg ttc gag gat atg | 96 |
|---|---|
| Asp Gln Val Leu Phe Val Asp Lys Arg Gln Pro Val Phe Glu Asp Met | |
|                 20                  25                  30 | |

| act gat att gat caa agt gcc agt gaa ccc cag acc aga ctg ata ata | 144 |
|---|---|
| Thr Asp Ile Asp Gln Ser Ala Ser Glu Pro Gln Thr Arg Leu Ile Ile | |
|         35                  40                  45 | |

| tac atg tac aaa gac agt gaa gta aga gga ctg gct gtg acc ctc tct | 192 |
|---|---|
| Tyr Met Tyr Lys Asp Ser Glu Val Arg Gly Leu Ala Val Thr Leu Ser | |
|     50                  55                  60 | |

| gtg aag gat agt aaa ayg tct acc ctc tcc tgt aag aac aag atc att | 240 |
|---|---|
| Val Lys Asp Ser Lys Xaa Ser Thr Leu Ser Cys Lys Asn Lys Ile Ile | |
| 65                  70                  75                  80 | |

| tcc ttt gag gaa atg gat cca cct gaa aat att gat gat ata caa agt | 288 |
|---|---|
| Ser Phe Glu Glu Met Asp Pro Pro Glu Asn Ile Asp Asp Ile Gln Ser | |
|                 85                  90                  95 | |

| gat ctc ata ttc ttt cag aaa cgt gtt cca gga cac aac aag atg gag | 336 |
|---|---|
| Asp Leu Ile Phe Phe Gln Lys Arg Val Pro Gly His Asn Lys Met Glu | |
|             100                 105                 110 | |

| ttt gaa tct tca ctg tat gaa gga cac ttt ctt gct tgc caa aag gaa | 384 |
|---|---|
| Phe Glu Ser Ser Leu Tyr Glu Gly His Phe Leu Ala Cys Gln Lys Glu | |
|         115                 120                 125 | |

| gat gat gct ttc aaa ctc att ctg aaa aaa aag gat gaa aat ggg gat | 432 |
|---|---|
| Asp Asp Ala Phe Lys Leu Ile Leu Lys Lys Lys Asp Glu Asn Gly Asp | |
|     130                 135                 140 | |

| aaa tct gta atg ttc act ctc act aac tta cat caa agt | 471 |
|---|---|
| Lys Ser Val Met Phe Thr Leu Thr Asn Leu His Gln Ser | |
| 145                 150                 155 | |

<210> SEQ ID NO 4
<211> LENGTH: 157
<212> TYPE: PRT
<213> ORGANISM: Mus sp.
<220> FEATURE:
<221> NAME/KEY: misc_feature
<222> LOCATION: (70)..(70)
<223> OTHER INFORMATION: The 'Xaa' at location 70
      stands for Thr, or Met.

<400> SEQUENCE: 4

Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
                20                  25                  30

Thr Asp Ile Asp Gln Ser Ala Ser Glu Pro Gln Thr Arg Leu Ile Ile

|       |       |       | 35    |       |       |       | 40    |       |       |       | 45    |       |       |
|-------|-------|-------|-------|-------|-------|-------|-------|-------|-------|-------|-------|-------|-------|

Tyr Met Tyr Lys Asp Ser Glu Val Arg Gly Leu Ala Val Thr Leu Ser
            50                      55                      60

Val Lys Asp Ser Lys Xaa Ser Thr Leu Ser Cys Lys Asn Lys Ile Ile
 65                  70                      75                      80

Ser Phe Glu Glu Met Asp Pro Pro Glu Asn Ile Asp Ile Gln Ser
                    85                      90                      95

Asp Leu Ile Phe Phe Gln Lys Arg Val Pro Gly His Asn Lys Met Glu
                   100                     105                     110

Phe Glu Ser Ser Leu Tyr Glu Gly His Phe Leu Ala Cys Gln Lys Glu
                115                     120                     125

Asp Asp Ala Phe Lys Leu Ile Leu Lys Lys Asp Glu Asn Gly Asp
            130                     135                     140

Lys Ser Val Met Phe Thr Leu Thr Asn Leu His Gln Ser
145                     150                     155

<210> SEQ ID NO 5
<211> LENGTH: 471
<212> TYPE: DNA
<213> ORGANISM: Homo sapiens
<220> FEATURE:
<221> NAME/KEY: CDS
<222> LOCATION: (1)..(471)
<223> OTHER INFORMATION: Xaa is isoleucine or threonine

<400> SEQUENCE: 5

```
tac ttt ggc aag ctt gaa tct aaa tta tca gtc ata aga aat ttg aat      48
Tyr Phe Gly Lys Leu Glu Ser Lys Leu Ser Val Ile Arg Asn Leu Asn
  1               5                  10                  15 gac caa gtt ctc ttc att gac caa gga aat cgg cct cta ttt gaa gat      96
Asp Gln Val Leu Phe Ile Asp Gln Gly Asn Arg Pro Leu Phe Glu Asp
             20                  25                  30 atg act gat tct gac tgt aga gat aat gca ccc cgg acc ata ttt att     144
Met Thr Asp Ser Asp Cys Arg Asp Asn Ala Pro Arg Thr Ile Phe Ile
         35                  40                  45 ata agt atg tat aaa gat agc cag cct aga ggt atg gct gta act atc     192
Ile Ser Met Tyr Lys Asp Ser Gln Pro Arg Gly Met Ala Val Thr Ile
     50                  55                  60 tct gtg aag tgt gag aaa att tca ayt ctc tcc tgt gag aac aaa att     240
Ser Val Lys Cys Glu Lys Ile Ser Xaa Leu Ser Cys Glu Asn Lys Ile
 65                  70                  75                  80 att tcc ttt aag gaa atg aat cct cct gat aac atc aag gat aca aaa     288
Ile Ser Phe Lys Glu Met Asn Pro Pro Asp Asn Ile Lys Asp Thr Lys
                 85                  90                  95 agt gac atc ata ttc ttt cag aga agt gtc cca gga cat gat aat aag     336
Ser Asp Ile Ile Phe Phe Gln Arg Ser Val Pro Gly His Asp Asn Lys
            100                     105                     110 atg caa ttt gaa tct tca tca tac gaa gga tac ttt cta gct tgt gaa     384
Met Gln Phe Glu Ser Ser Ser Tyr Glu Gly Tyr Phe Leu Ala Cys Glu
        115                     120                     125 aaa gag aga gac ctt ttt aaa ctc att ttg aaa aaa gag gat gaa ttg     432
Lys Glu Arg Asp Leu Phe Lys Leu Ile Leu Lys Lys Glu Asp Glu Leu
    130                     135                     140 ggg gat aga tct ata atg ttc act gtt caa aac gaa gac                 471
Gly Asp Arg Ser Ile Met Phe Thr Val Gln Asn Glu Asp
145                     150                     155
```

<210> SEQ ID NO 6
<211> LENGTH: 157
<212> TYPE: PRT

```
<213> ORGANISM: Homo sapiens
<220> FEATURE:
<221> NAME/KEY: misc_feature
<222> LOCATION: (73)..(73)
<223> OTHER INFORMATION: The 'Xaa' at location 73
      stands for Thr, or Ile.

<400> SEQUENCE: 6

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
50                  55                  60

Ser Val Lys Cys Glu Lys Ile Ser Xaa Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Glu Asp Glu Leu
    130                 135                 140

Gly Asp Arg Ser Ile Met Phe Thr Val Gln Asn Glu Asp
145                 150                 155

<210> SEQ ID NO 7
<211> LENGTH: 1120
<212> TYPE: DNA
<213> ORGANISM: Homo sapiens
<220> FEATURE:
<221> NAME/KEY: CDS
<222> LOCATION: (178)..(756)
<223> OTHER INFORMATION: Xaa is isoleucine or threonine

<400> SEQUENCE: 7
gcctggacag tcagcaagga attgtctccc agtgcatttt gccctcctgg ctgccaactc      60
tggctgctaa agcggctgcc acctgctgca gtctacacag cttcgggaag aggaaaggaa     120
cctcagacct tccagatcgc ttcctctcgc aacaaactat ttgtcgcagg aataaag        177 atg gct gct gaa cca gta gaa gac aat tgc atc aac ttt gtg gca atg       225
Met Ala Ala Glu Pro Val Glu Asp Asn Cys Ile Asn Phe Val Ala Met
1               5                   10                  15 aaa ttt att gac aat acg ctt tac ttt ata gct gaa gat gat gaa aac       273
Lys Phe Ile Asp Asn Thr Leu Tyr Phe Ile Ala Glu Asp Asp Glu Asn
            20                  25                  30 ctg gaa tca gat tac ttt ggc aag ctt gaa tct aaa tta tca gtc ata       321
Leu Glu Ser Asp Tyr Phe Gly Lys Leu Glu Ser Lys Leu Ser Val Ile
        35                  40                  45 aga aat ttg aat gac caa gtt ctc ttc att gac caa gga aat cgg cct       369
Arg Asn Leu Asn Asp Gln Val Leu Phe Ile Asp Gln Gly Asn Arg Pro
50                  55                  60 cta ttt gaa gat atg act gat tct gac tgt aga gat aat gca ccc cgg      417
Leu Phe Glu Asp Met Thr Asp Ser Asp Cys Arg Asp Asn Ala Pro Arg
65                  70                  75                  80 acc ata ttt att ata agt atg tat aaa gat agc cag cct aga ggt atg      465
Thr Ile Phe Ile Ile Ser Met Tyr Lys Asp Ser Gln Pro Arg Gly Met
```

-continued

```
                            85                  90                  95
gct gta act atc tct gtg aag tgt gag aaa att tca ayt ctc tcc tgt      513
Ala Val Thr Ile Ser Val Lys Cys Glu Lys Ile Ser Xaa Leu Ser Cys
                100                 105                 110 gag aac aaa att att tcc ttt aag gaa atg aat cct cct gat aac atc      561
Glu Asn Lys Ile Ile Ser Phe Lys Glu Met Asn Pro Pro Asp Asn Ile
            115                 120                 125 aag gat aca aaa agt gac atc ata ttc ttt cag aga agt gtc cca gga      609
Lys Asp Thr Lys Ser Asp Ile Ile Phe Phe Gln Arg Ser Val Pro Gly
        130                 135                 140 cat gat aat aag atg caa ttt gaa tct tca tca tac gaa gga tac ttt      657
His Asp Asn Lys Met Gln Phe Glu Ser Ser Ser Tyr Glu Gly Tyr Phe
145                 150                 155                 160 cta gct tgt gaa aaa gag aga gac ctt ttt aaa ctc att ttg aaa aaa      705
Leu Ala Cys Glu Lys Glu Arg Asp Leu Phe Lys Leu Ile Leu Lys Lys
                165                 170                 175 gag gat gaa ttg ggg gat aga tct ata atg ttc act gtt caa aac gaa      753
Glu Asp Glu Leu Gly Asp Arg Ser Ile Met Phe Thr Val Gln Asn Glu
            180                 185                 190 gac tagctattaa aatttcatgc cgggcgcagt ggctcacgcc tgtaatccca           806
Asp gcccttcggg aggctgaggc gggcagatca ccagaggtca ggtgttcaag accagcctga    866
ccaacatggt gaaacctcat ctctactaaa aatactaaaa attagctgag tgtagtgacg    926
catgccctca atcccagcta ctcaagaggc tgaggcagga gaatcacttg cactccggag    986
gtagaggttg tggtgagccg agattgcacc attgcgctct agcctgggca acaacagcaa   1046
aactccatct caaaaaataa aataaataaa taaacaaata aaaattcat aatgtgaaaa   1106 aaaaaaaaaa aaaa                                                    1120

<210> SEQ ID NO 8
<211> LENGTH: 193
<212> TYPE: PRT
<213> ORGANISM: Homo sapiens
<220> FEATURE:
<221> NAME/KEY: misc_feature
<222> LOCATION: (109)..(109)
<223> OTHER INFORMATION: The 'Xaa' at location 109
      stands for Thr, or Ile.

<400> SEQUENCE: 8

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Xaa Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
```

```
            130                 135                 140
His Asp Asn Lys Met Gln Phe Glu Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp

<210> SEQ ID NO 9
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: n is a, c, t, or g.

<400> SEQUENCE: 9
atrtcrtcda trttytcngg                                          20

<210> SEQ ID NO 10
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: n is a, c, t, or g.

<400> SEQUENCE: 10
ttygargaya tgacngayat                                          20

<210> SEQ ID NO 11
<211> LENGTH: 17
<212> TYPE: DNA
<213> ORGANISM: Artificial Sequence
<220> FEATURE:
<223> OTHER INFORMATION: Synthetic

<400> SEQUENCE: 11
ttygargara tggaycc                                             17

<210> SEQ ID NO 12
<211> LENGTH: 26
<212> TYPE: DNA
<213> ORGANISM: Artificial Sequence
<220> FEATURE:
<223> OTHER INFORMATION: Synthetic

<400> SEQUENCE: 12
cgagggatcc tactttggca agcttg                                   26

<210> SEQ ID NO 13
<211> LENGTH: 26
<212> TYPE: DNA
<213> ORGANISM: Artificial Sequence
<220> FEATURE:
<223> OTHER INFORMATION: Synthetic

<400> SEQUENCE: 13
```

```
caaggaattc ctagtcttcg gttttg                                        26
```

```
<210> SEQ ID NO 14
<211> LENGTH: 10
<212> TYPE: PRT
<213> ORGANISM: Homo sapiens

<400> SEQUENCE: 14

Tyr Phe Gly Lys Leu Glu Ser Lys Leu Ser
1               5                   10

<210> SEQ ID NO 15
<211> LENGTH: 10
<212> TYPE: PRT
<213> ORGANISM: Homo sapiens

<400> SEQUENCE: 15

Ser Ile Met Phe Thr Val Gln Asn Glu Asp
1               5                   10

<210> SEQ ID NO 16
<211> LENGTH: 14
<212> TYPE: PRT
<213> ORGANISM: Homo sapiens

<400> SEQUENCE: 16

Thr Ile Phe Ile Ile Ser Met Tyr Lys Asp Ser Gln Pro Arg
1               5                   10

<210> SEQ ID NO 17
<211> LENGTH: 17
<212> TYPE: PRT
<213> ORGANISM: Homo sapiens

<400> SEQUENCE: 17

Ile Ile Ser Phe Lys Glu Met Asn Pro Pro Asp Asn Ile Lys Asp Thr
1               5                   10                  15

Lys

<210> SEQ ID NO 18
<211> LENGTH: 50
<212> TYPE: PRT
<213> ORGANISM: Homo sapiens

<400> SEQUENCE: 18

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser
    50

<210> SEQ ID NO 19
<211> LENGTH: 13
<212> TYPE: PRT
<213> ORGANISM: Homo sapiens

<400> SEQUENCE: 19

Tyr Phe Gly Lys Leu Glu Ser Lys Leu Ser Val Ile Arg
1               5                   10
```

```
<210> SEQ ID NO 20
<211> LENGTH: 11
<212> TYPE: PRT
<213> ORGANISM: Artificial Sequence
<220> FEATURE:
<223> OTHER INFORMATION: Synthetic

<400> SEQUENCE: 20

Met Tyr Phe Gly Lys Leu Glu Ser Lys Leu Ser
 1               5                  10

<210> SEQ ID NO 21
<211> LENGTH: 34
<212> TYPE: DNA
<213> ORGANISM: Artificial Sequence
<220> FEATURE:
<223> OTHER INFORMATION: Synthetic

<400> SEQUENCE: 21
atagaattca aatgtacttt ggcaagcttg aatc                              34

<210> SEQ ID NO 22
<211> LENGTH: 27
<212> TYPE: DNA
<213> ORGANISM: Artificial Sequence
<220> FEATURE:
<223> OTHER INFORMATION: Synthetic

<400> SEQUENCE: 22
ataaagcttc tagtcttcgt tttgaac                                     27
```